United States Patent [19]

Wasmoen et al.

[11] Patent Number: 5,656,275
[45] Date of Patent: Aug. 12, 1997

[54] RECOMBINANT RACCOON POX VIRUS COMPRISING THE DNA ENCODING THE NUCLEOCAPSID PROTEIN OF FELINE INFECTIOUS PERITONITIS VIRUS

[75] Inventors: Terri Wasmoen; Lloyd Chavez; Hsien-Jue Chu, all of Fort Dodge, Iowa

[73] Assignee: American Home Products Corporation, Madison, N.J.

[21] Appl. No.: 480,882

[22] Filed: Jun. 7, 1995

Related U.S. Application Data

[63] Continuation of Ser. No. 125,516, Sep. 22, 1993, abandoned.

[51] Int. Cl.$^6$ .................... A61K 39/295; A61K 39/275; A61K 39/215; A61K 39/21; A61K 39/265; A61K 39/118; C12N 15/00; C12N 7/00; A61K 39/23; A61K 39/155; A61K 39/125

[52] U.S. Cl. .................... 424/199.1; 424/232.1; 424/221.1; 424/202.1; 424/201.1; 424/819; 424/207.1; 424/233.1; 424/211.1; 424/216.1; 424/208.1; 424/229.1; 424/263.1; 424/274.1; 435/320.1; 435/235.1

[58] Field of Search .................... 424/199.1, 232.1, 424/221.1, 202.1, 201.1, 819, 207.1, 233.1, 211.1, 119.1, 232, 216.1, 208.1, 229.1, 263.1, 274.1; 435/320.1, 235.1

[56] References Cited

U.S. PATENT DOCUMENTS 5,242,686 9/1993 Chu et al. .
5,266,313 11/1993 Esposito et al. .

FOREIGN PATENT DOCUMENTS 0376744 3/1990 European Pat. Off. .

*Primary Examiner*—Anthony C. Caputa
*Attorney, Agent, or Firm*—Darby & Darby

[57] ABSTRACT

This invention provides a recombinant raccoon poxvirus that expresses the nucleocapsid and transmembrane proteins of Feline Infectious Peritonitis Virus. The recombinant viruses are useful as vaccines, either alone or in combination with carriers and adjuvants.

9 Claims, 29 Drawing Sheets

FIG. 1A

```
         10              20              30              40
          *               *               *               *
ATG AAG TAC ATT TTG CTA ATA CTC GCG TGC ATA ATT GCA TGC GTT TAT
TAC TTC ATG TAA AAC GAT TAT GAG CGC ACG TAT TAA CGT ACG CAA ATA
 M   K   Y   I   L   L   I   L   A   C   I   I   A   C   V   Y>
 a   a   a   a   a    TRANSLATION OF FIPV E1  a   a   a   a   a 50              60              70              80              90
          *               *               *               *               *
GGT GAA CGC TAC TGT GCC ATG CAA GAC AGT CTG CAG GGC TTG CAG TGT ATT AAT
CCA CTT GCG ATG ACA CGG TAC GTT CTG TCA GAC GTC CCG AAC GTC ACA TAA TTA
 G   E   R   Y   C   A   M   Q   D   S   L   Q   G   L   Q   C   I   N>
 a   a   a   a   a    TRANSLATION OF FIPV E1  a   a   a   a   a 100             110             120             130             140
          *               *               *               *               *
GGC ACA AAT TCA AGA TGT CAA ACC TGC TTT GAA CGT GGT GAT CTT ATT
CCG TGT TTA AGT TCT ACA GTT TGG ACG AAA CTT GCA CCA CTA GAA TAA
 G   T   N   S   R   C   Q   T   C   F   E   R   G   D   L   I>
 a   a   a   a   a    TRANSLATION OF FIPV E1  a   a   a   a   a 150             160             170             180             190
          *               *               *               *               *
TGG CAT CTT GCT AAC TGG AAC TTC AGC TGG TCT GTA ATA TTG ATT GTT
ACC GTA GAA CGA TTG ACC TTG AAG TCG ACC AGA CAT TAT AAC TAA CAA
 W   H   L   A   N   W   N   F   S   W   S   V   I   L   I   V>
 a   a   a   a   a    TRANSLATION OF FIPV E1  a   a   a   a   a
```

FIG. 1B

```
         200             210             220             230             240
          *               *               *               *               *
TTT ATA ACA GTG TTA CAA TAT GGC AGA CCA CAA TTT AAA AGC TGG CTC GTT
AAA TAT TGT CAC AAT GTT ACC GGT GTT ACC TCG ACC GAG CAA
 F   I   T   V   L   Q   Y   G   R   P   Q   F   S   W   L   V>
 a   a   a   a   a           TRANSLATION OF FIPV E1   a   a   a   a   a  >

250             260             270             280
          *               *               *               *
TAT GGC ATT AAA ATG CTG ATC ATG TGG CTA TTA TGG CCT ATT GTT CTA
ATA CCG GAA TTT TAC TAA TTA CGT ATG AGA CTC GTT CAA TAA CAA GAT
 Y   G   I   K   M   L   I   M   W   L   L   W   P   I   V   L>
 a   a   a   a   a           TRANSLATION OF FIPV E1   a   a   a   a   a  >

290             300             310             320             330
          *               *               *               *               *
GCG CTT ACG ATT TTT AAT GCA TAC TCT GAG TAC CAA GTT TCC AGA TAT
CGC GAA TGC AAG CCG TAA ATT ACG TAG AGA CTC ATG GTT CAA AGG TCT ATA
 A   L   T   I   F   N   A   Y   S   E   Y   Q   V   S   R   Y>
 a   a   a   a   a           TRANSLATION OF FIPV E1   a   a   a   a   a  >

340             350             360             370             380
          *               *               *               *               *
GTA ATG TTC GGC TTT AGT GTT GCA GGT GCA GTT ACG TTT GCA CTT
CAT TAC AAG CCG AAA TCA CAA CGT CCA CGT CAA CAT TGC AAA CGT GAA
 V   M   F   G   F   S   V   A   G   A   V   T   F   A   L>
 a   a   a   a   a           TRANSLATION OF FIPV E1   a   a   a   a   a  >
```

FIG. 1C

```
        390              400              410              420              430
         *                *                *                *                *
TGG ATG ATG TAT TTT GTG AGA TCT GTT CAG CTA TAT AGA AGA ACC AAA
ACC TAC TAC ATA AAA CAC TCT AGA CAA GTC GAT ATA TCT TCT TGG TTT
 W   M   M   Y   F   V   R   S   V   Q   L   Y   R   R   T   K>
         a   a                    TRANSLATION OF FIPV E1 a   a   a   a   a >

440              450              460              470              480
         *                *                *                *                *
TCA TGG TGG TCT TTT AAT CCT GAG ACT AAT GCA ATT CTT TGT GTT AAT
AGT ACC ACC AGA AAA TTA GGA CTC TGA TTA CGT TAA GAA ACA CAA TTA
 S   W   W   S   F   N   P   E   T   N   A   I   L   C   V   N>
 a   a   a   a   a        TRANSLATION OF FIPV E1 a   a   a   a   a >

490              500              510              520
         *                *                *                *
GCA TTG GGT AGA AGT TAT GTG CTT CCC TTA GAT GGT ACT CCT ACA GGT
CGT AAC CCA TCT TCA ATA CAC GAA GGG AAT CTA CCA TGA GGA TGT CCA
 A   L   G   R   S   Y   V   L   P   L   D   G   T   P   T   G>
 a   a   a   a   a        TRANSLATION OF FIPV E1 a   a   a   a   a >

530              540              550              560              570
         *                *                *                *                *
GTT ACC CTT ACT CTA CTT TCA GGA AAT CTA GAT TAT GCT GAA GGT TTC AAA
CAA TGG GAA TGA GAT GAA AGT CCT TTA GAT CTA ATA CGA CTT CCA AAG TTT
 V   T   L   T   L   L   S   G   N   L   D   Y   A   E   G   F   K>
 a   a   a   a   a        TRANSLATION OF FIPV E1 a   a   a   a   a >
```

FIG. 1D

```
          580                590                600                610                620
           *                  *                  *                  *                  *
ATG GCT GGT GGT TTA ACC ATC GAG CAT TTG CCT AAA TAC GTC ATG ATT
TAC CGA CCA CCA AAT TGG TAG CTC GTA AAC GGA TTT ATG CAG TAC TAA
 M   A   G   G   L   T   I   E   H   L   P   K   Y   V   M   I >
 a   a   a   a   a   a   a   a   a   a  TRANSLATION OF FIPV E1

630                640                650                660                670
           *                  *                  *                  *                  *
GCT ACA CCT AGT A

FIG. 1E

```
          730              740              750              760
           *                *                *                *
GGT GAT TAC TCA ACA GAA GCA CGT ACT GAC AAT TTG AGT GAA CAT GAA
CCA CTA ATG AGT TGT CTT CGT GCA TGA CTG TTA AAC TCA CTT GTA CTT
 G   D   Y   S   T   E   A   R   T   D   N   L   S   E   H   E>
 a   a   a   a   a   a   a   a   a   a   a   a   a   a   a   a>    TRANSLATION OF FIPV E1

```
                 10            20            30            40
                 *             *             *             *
ATG GCC ACA CAG GGA CAA CGC GTC AAC TGG GGA GAT GAA CCT TCC AAA
TAC CGG TGT GTC CCT GTT GCG CAG TTG ACC CTA CTT GGA AGG TTT
 M   A   T   Q   G   Q   R   V   N   W   G   D   E   P   S   K>
 a   a   a   a         TRANSLATION OF FIPV                 a   a 50            60            70            80            90
                 *             *             *             *             *
AGA CGT GGT CGT TCT AAC CCC ATT ACC CTC GAA CAA GGA TCT AAA TTT TGG
TCT GCA CCA AGA TTG GGG TAA TGG GAG CTT GTT CCT AGA TTT AAA ACC
 R   R   G   R   S   N   P   I   T   L   E   Q   G   S   K   F   W>
 a   a   a   a         TRANSLATION OF FIPV                 a   a 100           110           120           130           140
                 *             *             *             *             *
TTG TCA TTC TAC AAC CCC ATT ACC CTC GAA CAA GGA TCT AAA TTT TGG
AAC AGT AAG ATG TTG GGG TAA TGG GAG CTT GTT CCT AGA TTT AAA ACC
 L   S   F   Y   N   P   I   T   L   E   Q   G   S   K   F   W>
 a   a   a   a         TRANSLATION OF FIPV                 a   a 150           160           170           180           190
                 *             *             *             *             *
AAT TTA TGT CCG AGA GAC CTT GTT CCC AAA GGA ATA GGT AAT AAG GAT
TTA AAT ACA GGC TCT CTG GAA CAA GGG TTT CCT TAT CCA TTA TTC CTA
 N   L   C   P   R   D   L   V   P   K   G   I   G   N   K   D>
 a   a   a   a         TRANSLATION OF FIPV                 a   a
```

FIG. 2B

```
        200         210         220         230         240
         *           *           *           *           *
CAA CAA ATT GGT TAT TGG AAT AGA CAG ATT CGT TAT CGT ATT GTA AAA
GTT GTT TAA CCA ATA ACC TTA TCT GTC TAA GCA ATA GCA TAA CAT TTT
 Q   Q   I   G   Y   W   N   R   Q   I   R   Y   R   I   V   K>
 a   a   a       TRANSLATION OF FIPV N   a   a   a   a   a   a>

250         260         270         280
         *           *           *           *
GGC CAG CGT AAG GAA C

FIG. 2C

```
           390         400         410         420         430
            *           *           *           *           *
ACT CGT GGA ACC AAT AAC GAA TCC AAA CCA CTG AGA TTT GAT GGT AAG
TGA GCA CCT TGG TTA TTG CTT AGG TTT GGT GAC TCT AAA CTA CCA TTC
 T   R   G   T   N   N   E   S   K   P   L   R   F   D   G   K>
 a   a   a   a       TRANSLATION OF FIPV N   a   a   a   a   a>

440         450         460         470         480
            *           *           *           *           *
ATA CCG CCA CAG TTT CAG CTT GAA GTG AAC CGT TCT AGG AAC AAT TCA
TAT GGC GGT GTC AAA GTC GAA CTT CAC TTG GCA AGA TCC TTG TTA AGT
 I   P   P   Q   F   Q   L   E   V   N   R

FIG. 2D

```
       530         540         550         560         570
        *           *           *           *           *
AGA GGA AGA CAC CAT TCC AAT AAC CAG AAT AAT AAT GTT GAG GAT ACA
TCT CCT GTG TCT AGG GTA TTG TCT AGG TTA TTA CAA CTC CTA TGT
 R   G   R   H   H   S   N   N   Q   N   N   N   V   E   D   T>
 a   a   a    TRANSLATION OF FIPV N  a   a   a   a   a   a   a>

580         590         600         610         620
        *           *           *           *           *
ATT GTA GCC GTG CTT GAA AAA TTA GGT GTT ACT GAC AAA CAA AGG TCA
TAA CAT CGG CAC GAA CTT TTT AAT CCA CAA TGA CTG TTT GTT TCC AGT
 I   V   A   V   L   E   K   L   G   V   T   D   K   Q   R   S>
 a   a   a    TRANSLATION OF FIPV N  a   a   a   a   a   a   a>

630         640         650         660         670
        *           *           *           *           *
CGT TCT AAA CCT AGA GAA CGT AGT GAT TCC AAA CCT AGG GAC ACA ACA
GCA AGA TTT GGA TCT CTT GCA TCA CTA AGG TTT GGA TCC CTG TGT TGT
 R   S   K   P   R   E   R   S   D   S   K   P   R   D   T   T>
 a   a   a    TRANSLATION OF FIPV N  a   a   a   a   a   a   a>

680         690         700         710         720
        *           *           *           *           *
CCT AAG AAT GCC AAC ACC TGG AAG AAA ACT GCA GGC AAG GGA
GGA TTC TTA CGG TTG TGG TTT GTG TTC TTT TGA CGT TCC CCT
 P   K   N   A   N   T   W   K   K   T   A   G   K   G>
 a   a   a    TRANSLATION OF FIPV N  a   a   a   a   a>
```

FIG. 2E

```
              730           740           750           760
               *             *             *             *
GAT GTG ACA ACT TTC TAT GCT AGA AGT AGT TCA GCT AAC TTT GGT
CTA CAC TGT TGA AAG ATA CGA TCT TCA TCA AGT CGA TTG AAA CCA
 D   V   T   T   F   Y   G   A   R   S   S   S   A   N   F   G>
 a   a   a   a       TRANSLATION OF FIPV N   a   a   a   a   a 770           780           790           800           810
   *             *             *             *             *
GAT AGT GAT CTC GTT GCC AAT GGT AAC GCT GCC AAA TGC TAC CCT CAG
CTA TCA CTA GAG CAA CGG TTA CCA TTG CGA CGG TTT ACG ATG GGA GTC
 D   S   D   L   V   A   N   G   N   A   A   K   C   Y   P   Q>
 a   a   a   a       T

FIG. 2F

```
            920         930         940         950         960
              *           *           *           *           *
ACC TAC TAC CTG CCA AAG GAT GAT GCC AAA ACT AGT CAA TTC CTA GAA
TGG ATG ATG GAC GGT TTC CTA CGG TTT TGA TCA GTT AAG GAT CTT
 T   Y   Y   L   P   K   D   D   A   K   T   S   Q   F   L   E>
 a   a   a   a   a   TRANSLATION OF FIPV N   a   a   a   a   a>

970         980         990        1000
              *           *           *           *
CAG ATT GAC GCT TAC AAG CGA CCT TCT GAA GTG GCT AAG GAT CAG AGG
GTC TAA CTG CGA ATG TTC GCT GGA AGA CTT CAC CGA TTC CTA GTC TCC
 Q   I   D   A   Y   K   R   P   S   E   V   A   K   D   Q   R>
 a   a   a   a   a   TRANSLATION OF FIPV N   a   a   a   a   a>

1010        1020        1030        1040        1050
              *           *           *           *           *
CAA AGA AGA TCC CGT TCT AAG TCT GCT GAT AAG AAG CCT GAG GAG TTG
GTT TCT TCT AGG GCA AGA TTC AGA CGA CTA TTC TTC GGA CTC CTC AAC
 Q   R   R   S   R   S   K   S   A   D   K   K   P   E   E   L>
 a   a   a   a   a   TRANSLATION OF FIPV N   a   a   a   a   a>
```

FIG. 2G

```
1060          1070          1080          1090          1100
 *             *             *             *             *
TCT GTA ACT CTT GTG GAG GCA TAC ACA GAT GTG TTT GAT GAC ACA CAG
 S   V   T   L   V   E   A   Y   T   D   V   F   D   D   T   Q>
 a   a   a   a   a   a   a   a   TRANSLATION OF FIPV N a a a a >

AGA CAT TGA GAA CAC CTC CGT ATG CTA CTA CAC AAA CTA CTG TGT GTC
 R   H   *                                                      
         1110          1120          1130
          *             *             *
GTT GAG ATG ATT GAT GAG GTT ACG AAC TAA
 V   E   M   I   D   E   V   T   N   *>
 a   TRANSLATION OF FIPV N a a a a a a >

CAA CTC TAC TAA CTA CTC CAA TGC TTG ATT
```

FIG. 5A

```
   1  CGAAAGGGCC TCGTGATACG CCTATTTTA  TAGTTAAATG  TCATGATAAT  AATGTTTCT
  61  TAGACGTCAG GTGGCACTTT TCGGGAAAT   GTGCGCGGAA  CCCCTATTTG  TTTATTTTC
 121  TAAATACATT CAAATATGTA TCCGCTCATG  AGACAATAAC  CCTGATAAAT  GCTTCAATAA
 181  TATTGAAAAA GGAAGAGTAT GAGTATTCAA  CATTTCCGTG  TCGCCCTTAT  TCCCTTTTT
 241  GCGGCATTTT GCCTTCCTGT TTTTGCTCAC  CCAGAAACGC  TGGTGAAAGT  AAAAGATGCT
 301  GAAGATCAGT TGGGTGCACG AGTGGGTTAC  ATCGAACTGG  ATCTCAACAG  CGGTAAGATC
 361  CTTGAGAGTT TTCGCCCCGA AGAACGTTTT  CCAATGATGA  GCACTTTTAA  AGTTCTGCTA
 421  TGTGGCGCGG TATTATCCCG TATTGACGCC  GGGCAAGAGC  AACTCGGTCG  CCGCATACAC
 481  TATTCTCAGA ATGACTTGGT TGAGTACTCA  CCAGTCACAG  AAAAGCATCT  TACGGATGGC
 541  ATGACAGTAA GAGAATTATG CAGTGCTGCC  ATAACCATGA  GTGATAACAC  TGCGGCCAAC
 601  TTACTTCTGA CAACGATCGG AGGACCGAAG  GAGCTAACCG  CTTTTTTGCA  CAACATGGGG
 661  GATCATGTAA CTCGCCTTGA TCGTTGGGAA  CCGGAGCTGA  ATGAAGCCAT  ACCAAACGAC
 721  GAGCGTGACA CCACGATGCC TGTAGCAAGT  GCAACAACT   ATTAACTGGC
 781  GAACTACTTA CTCTAGCTTC CCGGCAACAA  TTAATAGACT  GGATGGAGGC  GGATAAAGTT
 841  GCAGCACCAC TTCTGCGCTC GGCCCTTCCG  GCTGGCTGGT  TTATTGCTGA  TAAATCTGGA
 901  GCCGGTGAGC GTGGGTCTCG CGGTATCATT  GCAGCACTGG  GGCCAGATGG  TAAGCCCTCC
 961  CGTATCGTAG TTATCTACAC GACGGGGAGT  CAGGCAACTA  TGGATGAACG  AAATAGACAG
1021  ATCGCTGAGA TAGGTGCCTC ACTGATTAAG  CATTGGTAAC  TGTCAGACCA  AGTTACTCA
1081  TATATACTTT AGATTGATTT AAAACTTCAT  TTTTAATTTA  AAAGGATCTA  GGTGAAGATC
1141  CTTTTTGATA ATCTCATGAC CAAATCCCT   TAACGTGAGT  TTTCGTTCCA  CTGAGCGTCA
1201  GACCCCGTAG AAAAGATCAA AGGATCTCTT  TGAGATCCTT  TTTTTCTGCG  CGTAATCTGC
1261  TGCTTGCAAA CAAAAAAACC ACCGCTACCA  GCGGTGGTTT  GTTTGCCGGA  TCAAGAGCTA
1321  CCAACTCTTT TTCCGAAGGT AACTGGCTTC  AGCAGAGCGC  AGATACCAAA  TACTGTCCTT
1381  CTAGTGTAGC CGTAGTTAGG CCACCACTTC  AAGAACTCTG  TAGCACCGCC  TACATACCTC
1441  GCTCTGCTAA TCCTGTTACC AGTGGCTGCT  GCCAGTGGCG  ATAAGTCGTG  TCTTACCGGG
1501  TTGGACTCAA GACGATAGTT ACCGGATAAG  GCGCAGCGGT  CGGGCTGAAC  GGGGGGTCG
```

FIG. 5B

```
1561 TGCACACAGC CCAGCTTGGA GCGAACGACC TACACCGAAC TGAGATACCT ACAGCGTGAG
1621 CATTGAGAAA GCGCCACGCT TCCCGAAGGG AGAAAGGCGG CTTCCAGGGG ACAGGTATCC GGTAAGCGGC
1681 AGGGTCGGAA CAGGAGAGCG CACGAGGGAG CCTCTGACTT GAGCGTCGAT GAAACGCCTG GTATCTTTAT
1741 AGTCCTGTCG GGTTTCGCCA CCTCTGACTT GAGCGTCGAT TTTTGTGATG CTCGTCAGGG
1801 GGGCGGAGCC TATGGAAAAA CGCCAGCAAC GCGGCTTTT TACGGTTCCT GGCCTTTTGC
1861 TGGCCTTTTG CTCACATGTT CTTTCCTGCG TTATCCCCTG ATTCTGTGGA TAACCGTATT
1921 ACCGCCTTTG AGTGAGCTGA TACCGCTCGC CGCAGCCGAA CGACCGAGCG CAGCGAGTCA
1981 GTGAGCGAGG AAGCGGAAGA GCGCCCAATA CGCAAACCGC CTCTCCCCGC GCGTTGGCCG
2041 ATTCATTAAT GCAGCTGGCA CGACAGGTTT CCCGACTGGA AAGCGGGCAG TGAGCGCAAC
2101 GCAATTAATG TGAGTTAGCT CACTCATTAG GCACCCCAGG CTTTACACTT TATGCTTCCG
2161 GCTCGTATGT TGTGTGGAAT TGTGAGCGGA TAACAATTTC ACACAGGAAA CAGCTATGAC
2221 CATGATTACG CCAAGCTTTT GCGATCAATA AATGGATCAC AACCAGTATC TCTAACGAAT
2281 GTTCTTGCA GATGATGATT CATTTTTAA GTATTGGCT AGTCAAGATG ATGAAATCTT
2341 CATTATCTGA TATATTGCAA ATCACTCAAT ATCTAGACTT TCTGTTATTA TTATTGATCC
2401 AATCAAAAAA TAAATTAGAA GCCGTGGGTC ATTGTTATGA ATCTCTTTCA GAGGAATACA
2461 GACAATTGAC AAAATTCACA GACTTTCAAG ATTTAAAAA ACTGTTAAAC AAGGTCCCTA
2521 TTGTTACAGA TGGAAGGGTC AAACTTAATA AAGGATATTT GTTCGACTTT GTGATTAGTT
2581 CAAAAAGAA TCCTCTCTAG CTACCACCGC AATAGATCCT GTTAGATACA
2641 TAGATCCTCG TCGCAATATC GCATTTTCTA ACGTGATGGA TATATTAAAG TCGAATAATCG
2701 TGAACAATAA TTAATTCTTT ATTGTCATCA TGAACGATTT ACATATTCAG TTGATAATCG
2761 GCCCATGTT TTCAGTAAA AGTACAGAAT TAATTAGACG AGTTAGACGT TATCAAATAG
2821 CTCAATATAA ATGCGTGACT ATAAAATATT CTAACGATAA TAGATACGGA ACGGACTAT
2881 GGACGCATGA TAAGAATAAT TTTGAAGCAT TGGAAGCAAC TAAACTAGTT GATCTCTTGG
2941 AATCAATTAC AGATTTCTCC GTGATAGGTA TCGATGAAGG ACAGTTCTTT CCAGACATTG
3001 TTGAATTCCG AGCTTGGCTG CAGGTCGGGG ATCCCCCCTG CCCGGTTATT ATTATTTTTG
```

FIG. 5C

```
3061 ACACCAGACC AACTGGTAAT GGTAGGCGAAC GGGGCTCAGC TGAATTCCGC CGATACTGAC
3121 GGGCTCCAGG AGTCGTCGCC ACCAATCCCC ATATGGAAAC CGTCGATATT CAGCCATGTG
3181 CCTTCTTCCG CGTGCAGCAG ATGGCGATGG CTGGTTTCCA TCAGTTGCTG TTGACTGTAG
3241 CGGCTGATGT TGAACTGGAA GTCGCCGCGC CACTGGTGTG GGCCATAATT CAATTCGCGC
3301 GTCCCGCAGC GCAGACCGTT TTCGCTCGGG AAGACGTACG GGTATACAT GTCTGACAAT
3361 GGCAGATCCC AGCGGTCAAA ACAGGGCGCA GTAAGGCGGT CGGGATAGTT TTCTTGCGGC
3421 CCTAATCCGA GCCAGTTTAC CCGCTCTGCT ACCTGCGCCA GCTGGCAGTT CAGCCCAATC
3481 CGGCCCGGAT GCGGTGTATC GCTGCCACT TCAACATCAA CGGTAATCGC CATTGACCA
3541 CTACCATCAA TCCGGTAGGT TTTCCGGCTG ATAAATAAGG ATGCTGCCAC ATGCTGCCAC
3601 GCGTGACCGG TCGTAATCAG CACCGCATCA GCAAGTGTAT CTGCCGTGCA CTGCAACAAC
3661 GCTGCTTCGG CCTGGTAATG GCCCGCGCCG TTCCAGCGTT CGACCCAGGC GTTAGGGTCA
3721 ATGCGGGTCG CTTCACTTAC GCCAATGTCG TTATCCAGCG GTGCACGGGT GAACTGATCG
3781 CGCAGCGGCG TCAGCAGTTG TTTTTTATCG CCAATCCACA TCTGTGAAAG AAAGCCTGAC
3841 TGGCGGTTAA ATTGCCAACG CTTATTACCC AGCTCGATGC AAAAATCCAT TTCGCTGGTG
3901 GTCAGATGCG GGATGGCGTG GGAGCGGGCG GGGAGCGTCA CACTGAGGTT TTCCGCCAGA
3961 CGCCACTGCT GCCAGGCGCT GATGTGCCCG GCTTCTGACC ATGCGGTTCG GTTCGGTTGC
4021 ACTACGCGTA CTGTGAGCCA GAGTTGCCCG GCGCTCTCCG GCTGCGGTAG TTCAGGCAGT
4081 TCAATCAACT GTTACCTTG TGGAGCGACA TCCAGAGGCA CTTCACGCCT TGCCAGCGGC
4141 TTACCATCCA GCGCCACCAT CCAGTGCAGG AGCTCGTTAT CGCTATGACG GAACAGGTAT
4201 TCGCTGGTCA CTTCGATGGT TTGCCCGGAT AAACGGAACT GGAAAAACTG CTGCTGGTGT
4261 TTTGCTTCCG TCAGCGCTGG ATGCGGCGTG CGGTCGGCAA AGACCAGACC GTTCATACAG
4321 AACTGGCGAT CGTTCGGCGT ATGCGCCAAA TCACCGCCGT AAGCCGACCA CGGGTTGCCG
4381 TTTTCATCAT ATTTAATCAG CGACTGATCC ACCCAGTCCC AAGCGAAGCC GCCCTGTAAA
4441 CGGGATACT GACGAAACGC CTGCCAGTAT TTAGCCAGACT CGCCAAGACT GTTACCCATC
4501 GCGTGGGCGT ATTCGCAAAG GATCAGCGGG CGGTCTCTC CAGGTAGCGA AAGCCATTTT
4561 TTGATGGACC ATTCGGCAC AGCCGGGAAG GGCTGGTCTT CATCCACGCG CGGGTACATC
```

FIG. 5D

```
4621 GGGCAAATAA TATCGGTGGC CGTGGTGTCG GCTCCGCCGC CTTCATACTG CACCCGGGCGG
4681 GAAGGATCGA CAGATTTGAT CCAGCGTCGT AGCGCGTCGT GATTAGCGCC GTGGCCTGAT
4741 TCATTCCCCA GCGACCAGAT GATCACACTC GGGTGATTAC GATCGGGCTG CACCATTCGC
4801 GTTACGCGGT CGCTCATCGC CGGTAGCCAG CGCGGATCAT CGGTCAGACG ATTGATTGCC
4861 ACCATGCCGT GGGTTTCAAT ATTGGCTTCA TCCACCACAT ACAGGCCGTA GCGGTCGCAC
4921 AGCGTGTACC ACAGCGGATG GTTCGGATAA TGCGAACAGC GCACGGCGTT AAAGTTGTTC
4981 TGCTTCATCA GCAAGATATC CTGCACCATC GTGTGCTCAT CCATGACCTG ACCATGCAGA
5041 GGATGATGCT CGTGACGGTT AACGCCTTGA ATCAGCAACG GCTTGCCGTT CAGCAGCAGC
5101 AGACCATTTT CAATCCGCAC CTCGCGCGAA CCGACATCGC AGCCTTCTGC TTCGGCGCTC
5161 GTGCCGTCGG CGGTGTGCAG TTCAACCACC GCACGATAGA GATTCGGGAT TTCGGCGCTC
5221 CACAGTTTCG GGTTTTCGAC CTTGAGACGT AGTGTGACGC GATCGGCATA ACCACCACGC
5281 TCATCGATAA TTTCACCGCC GAAAGGCGCG GTGCCGTCGG CGACCTGCGT TTCACCCTGC
5341 CATAAAGAAA CTGTACCCG TAGGTAGTCA CGCACATCGC CGCACATCTG AACTTCAGCC
5401 TCCAGTACAG CGCGGCTGAA ATCATCATTA AAGCGAGTGG CAACATGAA ATCGCTGATT
5461 TGTGTAGTCG GTTTATGCAG CAACGAGACG TCACGGAAAA TGCCGCTCAT CCGCCACATA
5521 TCCTGATCTT CCAGATAACT GCGGTCACTC CAACGCAGCA CCATCACCGC GAGGCGGTTT
5581 TCTCCGGCGC GTAAAATGC GCTCAGTTCA AATTCAGACG GCAAACGACT GTCCTGGCCG
5641 TAACCGACCC GCACGCCCGT GCACCACAGA TGAAACGCCG AGTTAACGCC ATCAAAAATA
5701 ATTCGCGTCT GGCCTTCCTG TAGCCAGCTT TCATCAACAT TAAATGTGAG CGAGTAACAA
5761 CCCGTCGGAT TCTCCGTGGG AACAAACGGC GGATTGACCG TAATGGATA GGTTACGTTG
5821 GTGTAGATGG GCGCATCGTA ACCGTGCATC TGCCAGTTTG AGGGACGAC GACAGTATCG
5881 GCCTCAGGAA GATCGCACTC CAGGCCTTT TCCGGCACCG CTTCTGTGC CGGAAACCAG
5941 GCAAAGCGCC ATTCGCCATT CAGGCTGCGC AACTGTTGGG AAGGGCGATC GGTGCGGGCC
6001 TCTTCGCTAT TACGCCAGCT CAGGGTGCTG GATGTGCTTG CAAGGCGATT AAGTTGGGTA
6061 ACGCCAGGGT TTTCCCAGTC ACGACGTTGT AAAACGACGG GATCCCTCGA GGAATTCATT
```

FIG. 5E

```
6121  TATAGCATAG  AAAAAAACAA  AATGAAATC   TACTATATT   TTACATACAT  ATATTCTAAA
6181  TATGAAAGTG  GTGATTGTGA  CTAGCGTAGC  ATCGCTTCTA  GACATATACT  ATATAGTAAT
6241  ACCAATACTC  AAGACTACGA  AACTGATACA  ATCTCTTATC  ATGTGGGTAA  TGTTCTCGAT
6301  GTCGAATAGC  CATATGCCGG  TAGTTGCGAT  ATACATAAAC  TGATCACTAA  TTCCAAACCC
6361  ACCCGCTTTT  TATAGTAAGT  TTTTCACCCA  TAAATAATAA  ATACAATAAT  TAATTCTCTG
6421  TAAAAGTAGA  AAATATATTC  TAATTATTG   CACGGTAAGG  AAGTAGAATC  ATAAAGAACA
6481  GTGACGGATC  CCAATTCGGG  CATTTTTGT   TTGAACTAAA  CAAAATGAAG  TACATTTTGC
6541  TAATACTCGC  GTGCATAATT  GCATGCGTTT  ATGGTGAACG  CTACTGTGCC  ATGCAAGACA
6601  GTGGCTTGCA  GTGTATTAAT  GGCACAAATT  CAAGATGTCA  AACCTGCTTT  GAACGTGGTG
6661  ATCTTATTTG  GCATCTTGCT  AACTGGAACT  TCAGCTGGTC  TGTAATATTG  ATTGTTTTTA
6721  TAACAGTGTT  ACAATATGGC  AGACCACAAT  TTAGCTGGCT  CGTTTATGCC  ATTAAAATGC
6781  TGATCATGTG  GCTATTATGG  CCTATATGTC  TAGCGCTTAC  GATTTTTAAT  GCATACTCTG
6841  AGTACCAAGT  TTCCAGATAT  GTAAGTTCG   GCTTTAGTGT  TGCAGGTGCA  GTTGTAACGT
6901  TTGCACTTTG  GATGATGTAT  TTTGTGAGAT  CTGTTCAGCT  ATATAGAAGA  ACCAAATCAT
6961  GGTGTCTTT   TAATCCTGAG  ACTAATGCAA  TTCTTTTGTGT TAATGCATTG  GGTAGAAGTT
7021  ATGTGCTTCC  CTTAGATGGT  ACTCCTACAG  GTGTTACCCT  TACTCTACTT  TCAGGAAATC
7081  TATATGCTGA  AGTTTCAAA   ATGGCTGGTG  GTTAACCAT   CGAGCATTTG  CCTAAATACG
7141  TCATGATTGC  TACACCTAGT  AGAACCATCG  TTTATACATT  AGTTGGAAAA  CAATTAAAAG
7201  CAACTACTGC  CACAGGATGG  GCTTACTACG  TAAAATCTAA  AGCTGGTGAT  TACTCAACAG
7261  AAGCACGTAC  AGTACAATTTG  GAGCGTATGG  AGTGAACATG  ACATATGTG   TAACTAAACT
7321  TTCAAATGGG  GGAATTCTGT  GAGCGTATGG  CAAACGAAGG  AAAAATTAGT  TATAGTAGCC
7381  GCACTCGATG  GGACATTTCA  AGTACACCG   TTTAATAATA  TTTTGAATCT  TATTCCATTA
7441  TCTGAAATGG  TGGTAAAACT  AACTGCTGTG  TGTATGAAAT  GCTTTAAGGA  GGCTTCCTTT
7501  TCTAAACGAT  TGGGTGAGGA  AACCGAGATA  GAGGTAATGA  GAGGTAAGGA  TATGTATCAA
7561  TCGGTGTGTA  GAAAGTGTTA  CATCGACTCA  TAATATTATA  TTTTATCT    AAAAACTAA
```

FIG. 5F

```
7621 AAATAAACAT TGATTAAATT TTAATATAAT ACTTAAAAAT GGATGTGTG TCGTTAGATA
7681 AACCGTTTAT GTATTTTGAG GAAATTGATA ATGAGTTAGA TTACGAACCA GAAAGTGCAA
7741 ATGAGGTCGC AAAAAAACTG CCGTATCAAG GACAGTTAAA ACTATTACTA GGAGAATTAT
7801 TTTTCTTAG TAAGTTACAG CGACACGGTA TGCCACCGTA TTTCTATAAT GTGTATATAG
7861 GATCTGCTCC CGGTACACAT ATACGTTATT TGAGAGATCA TTTCTATAAT TTAGGAGTGA
7921 TCATCAAATG GATGCTAATT GACGGCCGCC ATCATGATCC TATTTTAAAT GGATTGCGTG
7981 ATGTGACTCT AGTGACTCGG TTCGTTGATG AGGAATATCT ACGATCCATC AAAAACAAC
8041 TGCATCCTTC TAAGATTATT TTAATTCTG ATGTGAGATC CAAACGAGGA GGAAATGAAC
8101 CTAGTACGGC GGATTACTA AGTAATTACG CTCTACAAAA TGTCATGATT AGTATTTAA
8161 ACCCGTGGC GTCTAGTCTT AAATGGAGAT GCCCGTTTCC AGATCAATGG ATCAAGGACT
8221 TTTATATCCC ACACGGTAAT AAATGTTAC AACCTTTTGC TCCTTCATAT TCAGGGCCGT
8281 CGTTTACAA CGTCGTGACT GGGAAAACCC TGGCGTTACC CAACTTAATC GCCTTGCAGC
8341 ACATCCCCT TTCGCCAGCT GGCGTAATAG CGAAGAGGCC CGCACCGATC GCCCTTCCCA
8401 ACAGTTGCGC AGCCTGAATG GCGAATGGCG CCTGATGCGG TATTTTCTCT TTACGCATCT
8461 GTGCGGTATT TCACACCGCA TATGGTGCAC TCTCAGTACC ATCTGCTCTG ATGCCGCATA
8521 GTTAAGCCAG TACACTCCGC TATCGCTACG TGACTGGGTC ATGGCTGCGC CCCGACACCC
8581 GCCAACACCC GCTGACGCGC CCTGACGGGC TTGTCTGCTC CCGGCATCCG CTTACAGACA
8641 AGCTGTGACC GTCTCCGGGA GCTGCATGTG TCAGAGGTTT TCACCGTCAT CACCGAAACG
8701 CGCGAGGCAG
```

FIG. 6A

```
   1 CGAAAGGGCC TCGTGATACG CCTATTTTA TAGGTTAATG TCATGATAAT AATGTTTCT
  61 TAGACGTCAG GTGGCACTTT TCGGGAAAT GTGCGCGGAA CCCTATTTG TTTATTTTC
 121 TAAATACATT CAAATATGTA TCCGCTCATG AGACAATAAC CCTGATAAAT GCTTCAATAA
 181 TATTGAAAAA GGAAGAGTAT GAGTATTCAA CATTTCCGTG TCGCCCTTAT TCCCTTTTTT
 241 GCGGCATTTT GCCTTCCTGT TTTTGCTCAC CCAGAAACGC TGGTGAAAGT AAAAGATGCT
 301 GAAGATCAGT TGGGTGCACG AGTGGGTTAC ATCGAACTGG ATCTCAACAG CGGTAAGATC
 361 CTTGAGAGTT TTCGCCCCGA AGAACGTTTT CCAATGATGA GCACTTTTAA AGTTCTGCTA
 421 TGTGGCGCGG TATTATCCCG TATTGACGCC GGGCAAGAGC AACTCGGTCG CCGCATACAC
 481 TATTCTCAGA ATGACTTGGT TGAGTACTCA CCAGTCACAG AAAAGCATCT TACGGATGGC
 541 ATGACAGTAA GAGAATTATG CAGTGCTGCC ATAACCATGA GTGATAACAC TGCGGCCAAC
 601 TTACTTCTGA CAACGATCGG AGGACCGAAG GAGCTAACCG CTTTTTTGCA CAACATGGG
 661 GATCATGTAA CTCGCCTTGA TCGTTGGGAA CCGGAGCTGA ATGAAGCCAT ACCAAACGAC
 721 GAGCGTGACA CCACGATGCC TGTAGCAATG GCAACAACGT TGCGCAAACT ATTAACTGGC
 781 GAACTACTTA CTCTAGCTTC CCGGCAACAA TTAATAGACT GGATGGAGGC GGATAAAGTT
 841 GCAGGACCAC TTCTGCGCTC GGCCCTTCCG GCTGGCTGGT TTATTGCTGA TAAATCTGGA
 901 GCCGGTGAGC GTGGGTCTCG CGGTATCATT GCAGCACTGG GGCCAGATGG TAAGCCCTCC
 961 CGTATCGTAG TTATCTACAC GACGGGGAGT CAGGCAACTA TGGATGAACG AAATAGACAG
1021 ATCGCTGAGA TAGGTGCCTC ACTGATTAAG CATTGGTAAC TGTCAGACCA AGTTTACTCA
1081 TATATACTTT AGATTGATTT AAAACTTCAT TTTTAATTTA AAAGGATCTA GGTGAAGATC
1141 CTTTTTGATA ATCTCATGAC CAAAATCCCT TAACGTGAGT TTTCGTTCCA CTGAGCGTCA
1201 GACCCCGTAG AAAAGATCAA AGGATCTCTT GAGATCCTTT TTTTCTGCGC GTAATCTGCG
1261 TGCTTGCAAA CAAAAAAACC ACCGCTACCA GCGGTGGTTT GTTTGCCGGA TCAAGAGCTA
1321 CCAACTCTTT TTCCGAAGGT AACTGGCTTC AGCAGAGCGC AGATACCAAA TACTGTCCTT
1381 CTAGTGTAGC CGTAGTTAGG CCACCACTTC AAGAACTCTG TAGCACCGCC TACATACCTC
1441 GCTCTGCTAA TCCTGTTACC AGTGGCTGCT GCCAGTGGCG ATAAGTCGTG TCTTACCGGG
1501 TTGGACTCAA GACGATAGTT ACCGGATAAG GCGCAGCGGT CGGGCTGAAC CGGGGGTTCG
```

FIG. 6B

```
1561 TGCACACAGC CCAGCTTGGA GCGAACGACC TACACCGAAC TGAGATACCT ACAGCGTGAG
1621 CATTGAGAAA GCGCCACGCT TCCCGAAGGG AGAAAGGCGG ACAGGTATCC GGTAAGCGGC
1681 AGGGTCGGAA CAGGAGAGCG CACGAGGGAG CTTCCAGGGG GAAACGCCTG CTCGTCAGGG
1741 AGTCCTGTCG GGTTTCGCCA CCCTCTGACTT GAGCGTCGAT TTTTGTGATG GCCCTTTGC
1801 GGGGGAGCC TATGAAAAA CGCCAGCAAC GCGGCCTTTT TACGGTCCT TAACCGTATT
1861 TGGCCTTTTG CTCACATGTT CTTCCTGCG TTATCCCTTG ATTCTGTGA CAGCGAGTCA
1921 ACCGCCTTTG AGTGAGCTGA TACCGCTCGC CGCAGCCGAA CGACCGAGCG CAGCGAGTCA
1981 GTGAGCGAGG AAGCGGAAGA GCGCCCAATA CGCAAACCGC CTCTCCCCGC GCGTTGGCCG
2041 ATTCATTAAT GCAGCTGGCA CGACAGGTTT CCCGACTGGA AAGCGGGCAG TGAGCGCAAC
2101 GCAATTAATG TGAGTTAGCT CACTCATTAG GCACCCCAGG CTTTACACTT TATGCTTCCG
2161 GCTCGTATGT TGTGTGGAAT TGTGAGCGGA TAACAATTTC ACACAGGAAA CAGCTATGAC
2221 CATGATTACG CCAAGCTTTT GCGATCAATA AATGATCAC AACCAGTATC TCTTAACGAT
2281 GTTCTTCGCA GATGATGATT CATTTTTAA GTATTGGCTT AGTCAAGATG ATGAAATCTT
2341 CATTATCTGA TATATTCTTA ATCACTCAAT ATCTAGACTT TCTGTTATTA TTATTGATCC
2401 AATCAAAAA TAAATTAGAA GCCGTGGGTC ATTGTTATGA ATCTCTTTCA GAGGAATACA
2461 GACAATTGAC AAAATTCACA GACTTTCAAG ACTTTTAAAA ACTGTTAACC AAGGTCCCTA
2521 TTGTTACAGA TGGAAGGGTC AAACTTAATA AAGGATATTT GTTGACTTT GTGATTAGTT
2581 CAAAAAAGAA CAAAAAGAA TCCCTCTCTAG AATAGATATA AATAGATCCT GTTAGATACA
2641 TAGATCCTCG TCGCAATATC GCATTTTCTA ACGTGATGGA CTACCACCGC TCGAATAATG
2701 TGAACAATAA TTAATTCATT ATGTCATCA AGTACAGATT ACATATTCAG TTGATAATCG
2761 GCCCCATGTT TTCAGTAAA AGTACAGATCG AGTTAGACGT AGTTAGACGT TATCAAATAG
2821 CTCAATATAA ATGCGTGACT ATAAAATATT CTAACGATAA TAGATACGGA ACGGGACTAT
2881 GGACGCATGA TAAGAATAAT TTGAAGCAT TGGAAGCAAC TAAACTATGT GATCTCTTGG
2941 AATCAATTAC AGATTTCTCC GTGATAGGTA TCGATGAAGG ACAGTTCTTT CCAGACATTG
3001 TTGAATTCCG AGCTTGGCTG CAGGTCGGGG ATCCCCCCTG CCCGGTTATT ATTATTTG
```

FIG. 6C

```
3061 ACACCAGACC AACTGGTAAT GGTAGGGAAC GGCGCTCAGC TGAATTCCGC CGATACTGAC
3121 GGGCTCCAGG AGTCGTCGCC ACCAATCCCC ATATGGAAAC CGTCGATATT CAGCCATGTG
3181 CCTTCTTCCG CGTGCAGCAG ATGGCGATGG CTGGTTTCCA TCAGTTGCTG TTGACTGTAG
3241 CGGCTGATGT TGAACTGGAA GTCGCCGCGC CACTGGTGTG GGCCATAATT CAATTCGCGC
3301 GTCCCGCAGC GCAGACCGTT TTGCTCGGG AAGACGTACG GGTATACAT GTCTGACAAT
3361 GGCAGATCCC AGCGGTCAAA ACAGGCGGCA GTAAGGCGGT CGGGATAGTT TCTTGCGGC
3421 CCTAATCCGA GCCAGTTTAC CCGCTCTGCT ACCTGCGCCA GCTGGCAGTT CAGGCCAATC
3481 CGGCCGGAT GCGGTGTATC GCTCGCCACT TCAACATCAA CGTGAATCGC CATTTGACCA
3541 CTACCATCAA TCCGGTAGTT TTTCCGGCTG ATAAATAAGG TTTTCCCCTG ATGCTGCCAC
3601 GCGTGACCGG TCGTAATCAG CACCGCATCA GCAAGTGTAT CTGCCGTGCA CTGCAACAAC
3661 GCTGCTTCGG CCTGGTAATG GCCCGCCGC TTCCAGCGTT CGACCCAGGC GTTAGGGTCA
3721 ATGCGGGTCG CCTCACTTAC GCCAATGTCG TTATCCAGCG GTGCACGGGT GAACTGATCG
3781 CGGAGCGGGA TCAGCAGTTG TTTTTATCG CCAATCCACA TCTGTGAAAG AAAGCCTGAC
3841 TGGCGGTTAA ATTGCCAACG CTTATTACCC AGCTCGATGC AAAAATCCAT TTGCTGTGTG
3901 GTCAGATGCG GGATGGCGTG GGACGCGGCG GGGAGCGTCA CACTGAGGTT TTCCGCCAGA
3961 CGCCACTGCT GCCAGGCGCT GATGTGCCCG GCTTCTGACC ATGCGGTCGC GTTCGGTTGC
4021 ACTACGCGTA CTGTGAGCCA GAGTTGCCCG GCGCTCTCCG GCTGCGGTAG TTCAGGCAGT
4081 TCAATCAACT GTTACCTTG TGGAGCGACA TCCAGAGGCA CTTCACCGCT TGCCAGCGGC
4141 TTACCATCCA GGCCACCAT CCAGTGCAGG AGCTCGTTAT CGCTATGACG GAACAGGTAT
4201 TCGCTGGTCA CTTCGATGT TTGCCCGGAT AAACGGAACT GGAAAAACTG CTGCTGGTGT
4261 TTTGCTTCCG TCAGCGCTGG ATGCGGCGTG CGGTCGGCAA AGACCAGACC GTTCATACAG
4321 AACTGGCGAT CGTTCGGCGT ATGCCAAAA TCACCGCCGT AAGCCGAGCA CGGGTTGCCG
4381 TTTTCATCAT ATTTAATCAG CGACTGATCC ACCCAGTCCC AGACGAAGCC GCCCGTAAA
4441 CGGGATACT GACGAAACGC CTGCCAGTAT TTAGCGAAAC CGCCAAGACT GTTACCCATC
4501 GCGTGGGCGT ATTCGCCAAAG GATCAGCGG CGGTCTCTC CAGGTAGCGA AAGCCATTTT
```

FIG. 6D

```
4561 TTGATGGACC ATTTCGCCAC AGCCGGGAAG GGCTGGTCTT CATCCACGCG CGCGTACATC
4621 GGGCAAATAA TATCGGTGGC CGTGGTGTCG GCTCCGCCGC CTTCATATCTG CACCGGGCCG
4681 GAAGGATCGA CAGATTTGAT CCAGCGATAC AGCGCGTCGT GATTAGCGCC GTGGCCTGAT
4741 TCATTCCCCA GCGACCAGAT GATCACACTC GGGTGATTAC GATCGCGCTG CACCATTCGC
4801 GTTACGCGTT CGCTCATCGC CGGTAGCCAG CGGTGATCAT CGGTCAGACG ATTGATTGGC
4861 ACCATGCCGT GGGTTTCAAT ATTGGCTTCA TCCACCACAT ACAGGCCGTA GCGGTCGCAC
4921 AGCGTGTACC ACAGCGGATG GTTCGGATAA TGCGAACAGC GCACGGCGTT AAGTTGTTC
4981 TGCTTCATCA GCAGGATATC CTGCACCATC GTCTGCTCAT CCATGACCTG ACCATGCAGA
5041 GGATGATGCT CGTGACGGTT AACGCCTCGA ATCAGCAACG GCTTGCCGTT CAGCAGCAGC
5101 AGACCATTTT CAATCCGCAC CTGCGCGAAA CCGACATCGC AGCTTCTCGC TTCAATCAGC
5161 GTGCCGTCGG CGGTGTGCAG TTCAACCACC GCACGATAGA GATTCGGGAT TTCGCGCTC
5221 CACAGTTTCG GGTTTTTCGA CTTGAGACGT AGTGTGACGC GATCGGCATA ACCACCACGC
5281 TCATCGATAA TTTCACCGCC GAAAGGCGCG GTGCCGCTGG CGACCTCCGT TTCACCCTGC
5341 CATAAAGAAA CTGTTACCCG TAGGTAGTCA CGCACATCTG AACTTCAGCC
5401 TCCAGTACAG CGCGGCTGAA ATCATCATTA AAGCGAGTGG CAACATGGAA ATCGCTGATT
5461 TGTGTAGTCG GTTATGCAG CAACGAGACG TGCCGCTCAT CCGCCACATA
5521 TCCTGATCTT CCAGATAACT GCCGTCACTC CAACGCAGCA CCATCACCGC GAGGCGGTTT
5581 TCTCCGGCGC GTAAAAATGC GCTCAGGTCA AATTCAGACG GCAAACGACT GTCCTGGCCG
5641 TAACCGACCC AGCGCCCGTT GCACCACAGA AGTTAACGCC ATCAAAAATA
5701 ATTCGGTCT GGCCTTCCTG TAGCCAGCTT TCATCAACAT TAAATGTGAG CGGTTACGTTG
5761 CCCGTCGAT TCTCCGTGGG AACAAACGGC GGATTGACCG TAATGGGATA GACAGTATCG
5821 GTGTAGATGG GCGCATCGTA ACCGTCACTC TGCCAGTTTG AGGGGACGAC CGGAAACCAG
5881 GCCTCAGGAA GATCGCACTC CAGGCCAGCT TCCGGCACCG CTTCGTGTGC GGTGCGGGCC
5941 GCAAAGCGCC ATTCGCCATT CAGGCTGCGC GGCGAAAGGG AAGGGCGATC AAGTTGGGTA
6001 TCTTCGCTAT TACGCCAGCT GGCGAAAGGG AACTGTTGCG CAAGGCGATT AAGTTGGGTA
6061 ACGCCAGGGT TTTCCCAGTC ACGACGTTGT AAAACGACGG GATCCCTCGA GAATTCATT
```

FIG. 6E

```
6121  TATAGCATAG AAAAAAACAA AATGAAATTC TACTATATTT TTACATACAT ATATTCTAAA
6181  TATGAAAGTG GTGATTGTGA CTAGCGTAGC ATCGCTTCTA GACATATACT ATATAGTAAT
6241  ACCAATACTC AAGACTACGA AACTGATACA ATCTCTTATC ATGTGGGTAA TGTTCTCGAT
6301  GTCGAATAGC CATATGCCGG TAGTTGCGAT ATACATAAAC TGATCACTAA TTCCAAACCC
6361  ACCCGCTTTT TATAGTAAGT TTTCACCCA TAAATAATAA ATACAATAAT TAATTTCTCG
6421  TAAAAGTAGA AAATATATTC TAATTTATTG CACGGTAAGG AAGTAGAATC ATAAAGAACA
6481  GTGACGGATC CCGGGATGGC CACACAGGA CAACGCGTCA ACTGGGGAGA TGAACTTCC
6541  AAAAGACGTG GTCGTTCTAA CTCTCGTGGT CGGAAGAATA ATGATATACC TTTGTCATTC
6601  TACAACCCCA TTACCCTCGA ACAAGGATCT AAATTTGGA ATTTATGTCC GAGAGACTT
6661  GTTCCCAAAG AATAGGTAA CAAATTGGTT CAAATTGGTT ATTGGAATAG ACAGATTCGT
6721  TATCGTATTG TAAAAGGCCA GCGTAAGAA CTCGCTGAGA GGTGGTTCTT TTACTTCTTA
6781  GGTACAGAGAC CTCATGCTGA TGCTAAATTC AAAGACAAGA TTGATGGAGT CTTCTTGGTT
6841  GCAAGGGATG GTGCCATGAA CAAGCCCACA ACGCTTGGCA CTCGTGAAC CAATAACGAA
6901  TCCAAACCAC TGAGATTTGA TGGTAAGATA CGGCCACAGT TTCAGCTTGA AGTGAACCGT
6961  TCTAGGAACA ATTCAAGGTC TGGTTCTCTG TCTAGATCTG TTTCAAGAAA CAGATCTCAA
7021  TCTAGAGGAA GACACCATTC CAATAACCAG AATAATAATG TTGAGGATAC AATTGTAGCC
7081  GTGCTTGAAA AATTAGGTGT TACTGACAAA CAAGGTCAC GTTCTAAACC TAGAGAACGT
7141  AGTGATTCCA AACCTAGGA TACTGCTTAC CACAACACCT AAGAATGCCA ACAAACACAC CTGGAAGAAA
7201  ACTGCAGGCA AGGGAGATGT GACAACTTTC TATGGTGCTA GAAGTAGTC AGCTAACTTT
7261  GGTGATAGTG ATCTCGTTGC CAATGGTAAC GCTGCCAAAT GCTACCCTCA GATAGCTGAA
7321  TGTGTTCCAT CAGTGTCTAG CATAATCTTT GGCAGTCAAT GGTCTGCTGA AGAAGCTGGT
7381  GATCAAGTGA AAGTCACGCT CACTCACACC TACTACCTGC CAAAGGATGA TGCCAAAACT
7441  AGTCAATTCC TAGAACAGAT TGACGCTTAC AAGCGACCTT TGAAGTGGC TAAGGATCAG
7501  AGGCAAAGAA GATCCCGTTC TAAGTCTGCT GATAAGAAGC CTGAGGAGTT GTCTGTAACT
7561  CTGTGGAGG CATACACAGA TGTGTTTGAT GACACACAGG TTGAGATGAT TGATGAGGTT
7621  ACGAACTAAA CGCATGCCCG GAATTCTGT GAGCGTATGG CAAACGAAGG AAAAATTAGT
```

FIG. 6F

```
7681 TATAGTAGCC GCACTCGATG GGACATTTCA ACGTAAACCG TTTAATAATA TTTTGAATCT
7741 TATTCCATTA TCTGAAATGG TGTAAAACT AACTGCTGTG TGTATGAAAT GCTTTAAGGA
7801 GGCTTCCTTT TCTAAACGAT TGGGTGAGGA AACCGAGATA GAAATAATAG GAGTAATGA
7861 TATGTATCAA TCGTGTGTA GAAAGTGTTA CATCGACTCA TAATATTATA TTTTTATCT
7921 AAAAAACTAA AAATAAACAT TGATTAAATT TTAATATAAT ACTTAAAAAT GGATGTGTG
7981 TCGTTAGATA AACCGTTTAT GTATTTTGAG GAAATTGATA ATGAGTTAGA TTACGAACCA
8041 GAAAGTGCAA ATGAGGTCGC AAAAAAACTG CCGTATCAAG GACAGTTAAA ACTATTACTA
8101 GGAGAATTAT TTTTTCTTAG TAAGTTACAG CGACACGGTA TATTAGATGG TGCCACCGTA
8161 GTGTATATAG GATCTGCTCC CGGTACACAT ATACGTTATT TGAGAGATCA TTTCTATAAT
8221 TTAGGAGTGA TCATCAAATG GATGCTAATT GACGGCCGCC ATCATGATCC TATTTTAAAT
8281 GGATTGCGTG ATGTGACTCT AGTGACTCGG TTCGTTGATG AGGAATATCT ACGATCCATC
8341 AAAAAACAAC TGCATCCTTC TAAGATTATT TTAATTTCTG AGTGAGATC CAAACGAGGA
8401 GGAAATGAAC CTAGTACGGC GGATTACTA AGTAATTACG CTCTACAAAA TGTCATGATT
8461 AGTATTTAA ACCCCGTTGC GTCTAGTCTT AAATGGAGAT GCCCGTTCC AGATCAATGG
8521 ATCAAGGACT TTTATATCCC ACACGTGTAAT AAAATGTTAC AACCTTTTGC TCCTTCATAT
8581 TCAGGGCCGT CGTTTTACAA CGTCGTGACT GGGAAAACCC TGGCGTTACC CAACTTAATC
8641 GCCTTGCAGC ACATCCCCCT TTCGCCAGCT GGCGTAATAG CGAAGAGGCC CGCACCGATC
8701 GCCCTTCCCA ACAGTTGCGC AGCCTGAATG GCGAATGGCG CCTGATGCGG TATTTTCTCT
8761 TTACGCATCT GTGCGGTATT TCACACCGCA TATGGTGCAC TCTCAGTACC ATCTGCTCTG
8821 ATGCCGCATA GTTAAGCCAG TACACTCCGC TATCGCTACG TGACTGGGTC ATGGCTGCGC
8881 CCCGACACCC GCCAACACCC GCTGACGCGC CCTGACGGGC TTGTCTGCTC CCGGCATCCG
8941 CTTACAGACA AGCTGTGACC GTCTCCGGGA GCTGCATGTG TCAGAGGTTT TCACCGTCAT
9001 CACCGAAACG CGCGAGGCAG
```

RECOMBINANT RACCOON POX VIRUS COMPRISING THE DNA ENCODING THE NUCLEOCAPSID PROTEIN OF FELINE INFECTIOUS PERITONITIS VIRUS

This is a continuation of application Ser. No. 08/125,516, filed Sep. 22, 1993, now abandoned.

FIELD OF THE INVENTION

The present invention pertains to the prophylaxis of disease caused by feline infectious peritonitis virus (FIPV), using recombinant raccoon pox viruses (RRPVs) expressing the nucleocapsid and transmembrane proteins of FIPV as vaccines.

BACKGROUND OF THE INVENTION

Feline infectious peritonitis virus (FIPV) induces a systemic infection in cats that is often fatal. The effusive form of the disease is characterized by accumulation of fibrinous ascitic fluid. The non-effusive form of the disease is characterized by granulomatous lesions in multiple organs including, but not limited to, liver, spleen, kidneys, lung, and intestines. Reviewed in Barlough, J. E. and C. A. Stoddart. Feline Coronaviral Infections in C. E. Greene (Ed.). *Infectious Diseases of the Dog and Cats.* W. B. Saunders Co., Philadelphia, Pa., 1990, pp. 300–312.

Feline infectious peritonitis virus is a coronavirus composed of three major structural proteins: The S (spike) protein, the E1 or M (transmembrane) protein, and the N (nucleocapsid) protein. Venema et al., Virology 181: 327–335, 1991 and Dale, et al., EPO 0,376,744.

Prior vaccines intended to prevent FIPV infection have actually been shown to exacerbate the disease caused by this virus. Pedersen, N. C. and J. W. Black, Am. J. Vet. Res. 44: 229–234, 1983; Vennema H., et al., J. Virol. 64: 1407–1409, 1990; Barlough, J. E., Can. J. Comp. Med. 49: 303–307, 1985; Barlough J. E. et al., Lab. Anim. Sci. 34: 592–597, 1984; Stoddart, C. A., et al., Res. Vet. Sci. 45: 383–388, 1988; and Pedersen, N. C., Adv. Vet. Sci. Comp. Med. 33: 413–428, 1989. This phenomenon apparently reflects an immune enhancement of infection mediated by immunoglobulins produced in response to the virus, in particular by those antibodies directed against the S protein. Olsen C. W. et al., J. Virol. 4: 175–189, 1981. Therefore, the best candidate vaccine for prophylaxis of this disease would be a preparation that induces strong cell-mediated immunity in the absence of enhancing antibodies. This could be accomplished with a vaccine that lacks the outer envelope protein but contains the other structural proteins of FIPV (N and E1). Prior attempts to vaccinate cats with a recombinant vaccinia virus expressing the N or E1 proteins of FIPV, however, have failed to induce strong protective immunity. Venema et al., Virology 181:327–335, 1991 and Dale, et al., European Patent Application 0,376,744. See also, Venema, European Patent Application 0,411,684.

What is needed in the art, therefore, is an effective vaccine against FIPV that utilizes the N and E1 proteins, or segments therefrom, as immunogens.

SUMMARY OF THE INVENTION

The present invention pertains to the induction of protective immunity to FIPV in cats. One object of the invention is to provide recombinant raccoon poxviruses containing the genes for the FIPV N or M/E1 proteins (RRPV-N and RRPV-E1, respectively).

A further object of the invention is to provide a feline vaccine comprising RRPV-N or RRPV-E1, either singly or in combination, or in combination with other viruses, bacteria, or fungi that have been inactivated or attenuated.

A still further object of the invention is to provide a method for preventing disease caused by FIPV, by administering to a feline in need of such treatment a vaccine comprising RRPV-N, RRPV-E1, or combinations thereof.

These and other objects and advantages, which will be apparent from this specification, are achieved by the invention described below.

DESCRIPTION OF THE DRAWINGS

FIGS. 1A through 1E, when joined at respective match lines A—A through D—D, illustrate the nucleotide and amino acid sequence of the FIPV E1 protein and the (SEQ ID NO: 1) and (SEQ ID NO: 5), respectively. (FIGS. 1A and 1B, respectively.)

FIGS. 2A through 2G, when joined at respective match lines A—A through F—F, illustrate the nucleotide and amino acid sequence of the FIPV N protein (SEQ ID NO: 2) and (SEQ ID NO:6), respectively.

FIGS. 5A to 5F, when joined at respective match lines A—A through E—E, illustrate the nucleotide sequence of pSC11 FIPV E1.

FIGS. 6A through 6F, when joined at respective match lines A—A through E—E, illustrate the nucleotide sequence of pSC11 FIPV N.

DETAILED DESCRIPTION OF THE INVENTION

Figure 3A:
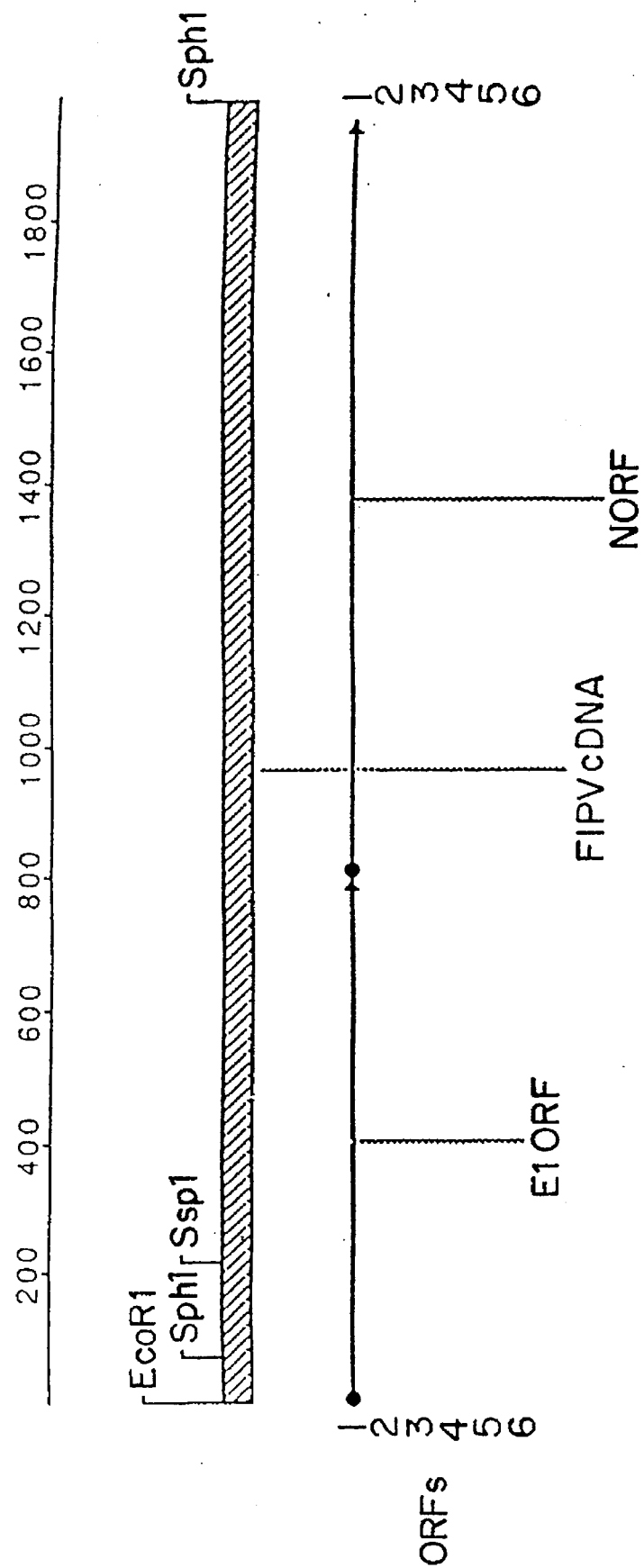
FIGS. 3A and 3B illustrate the plasmid used to clone the genes encoding the FIPV E1 and N proteins.

The vaccine of the present invention may be prepared by creating recombinant raccoon poxviruses (RRPVs) containing the genes encoding the N or E1 proteins of FIPV or immunogenic fragments thereof. These genes are first inserted into a transfer plasmid, which is then introduced into appropriate host cells that have been previously infected with a raccoon poxvirus. As a result, the DNA from the transfer plasmid is incorporated into the poxvirus DNA by homologous recombination, producing the RRPVs that are released from the cells.

DNA encoding the FIPV N or E1 proteins is inserted into the transfer plasmid immediately downstream of a poxvirus promoter. In a preferred embodiment, the early/late 7.5 Kd protein promoter of vaccinia virus is used; however, alternate promoter elements that are functional in poxviruses can also be used.

The preferred transfer plasmid also contains a beta-galactosidase marker gene, which allows for selection and detection of the plasmid DNA sequences in recombinant viruses. It will be obvious to one skilled in the art that alternative selectable marker genes, such as the neomycin resistance gene or the *E. coli* gpt gene or others, can be used to practice the invention. Flanking the foreign gene of interest and the selectable marker gene are thymidine kinase DNA sequences, which facilitate recombinatorial integration of the plasmid DNA sequences into the raccoon poxvirus DNA.

Recombinant viruses expressing the FIPV N or E1 genes are prepared by first infecting a susceptible cell line such as Vero (ATCC CCL 81), BSC-1 (ATCC CCL 26), RAT-2 (ATCC CRL 1764), or CRFK (ATCC CCL 941) with wild type raccoon poxvirus (ATCC VR-838 or similar isolates, such as, for example, RCNV71-I-85A). Transfer plasmid DNA containing the E1 or N gene is then transfected into the infected cells using cationic liposome-mediated transfection, or other suitable techniques such as electroporation or calcium phosphate precipitation. Virus replication is allowed to proceed until cytopathic effects are noted in all cells.

Incorporation of the FIPV E1 or N genes into poxvirus DNA is accompanied by disruption of the viral thymidine kinase gene. Therefore, virus harvested from this infection may be isolated by selecting for the absence of a thymidine kinase gene; this is achieved by growth on tk-RAT-2 cells (ATCC CRL 1764) in the presence of 5-bromodeoxyuridine. Viruses containing a gene insert from the transfer plasmid are further identified by the appearance of a blue plaque color when grown in the presence of a chromogenic substrate for beta-galactosidase such as X-gal.

Viral plaques that survive these selection and screening procedures are then subjected to several cycles of plaque purification. Subsequently, the presence of the E1 or N genes is confirmed by polymerase chain reaction technology, and the presence of E1 or N protein is confirmed by immunoblot analysis using specific antibodies. These viruses are designated RRPV-FIPV E1 and RRPV-FIPV N, respectively.

In a further embodiment of the present invention, the genes encoding N and E1 were inserted into a single transfer plasmid. Introduction of this plasmid into cells previously infected with wild-type raccoon poxvirus results in the production of recombinant viruses that express both proteins simultaneously (RRPV-FIPV E1/N).

In a still further embodiment, RRPVs can be produced that express less-than-full-length segments of the FIPV E and N proteins. The techniques used to engineer transfer plasmids encoding partial sequences of E1 and N are well-known and widely used in the art, as are the methods for production and screening of RRPVs as detailed in this specification. For example, introduction of oligonucleotides containing a stop codon at various points along E1 or N DNA will produce a nested set of carboyxterminal-truncated versions of that gene, which can then be incorporated into RRPVs. It will be apparent to one of ordinary skill in the art that systematic screening of such recombinant RRPVs can establish whether the intact protein, or subfragments thereof, are most preferred in practicing the present invention. Furthermore, as stated above, DNA encoding different fragments of E1 and N can be used in a combination vaccine after incorporation into the same, or different, RRPVs.

For vaccine preparation, susceptible cells such as those listed above are infected with RRPVs at a multiplicity Of infection (MOI) of 0.1 infectious units/cell or less. In this specification, an infectious unit is defined as a Tissue Culture Infectious Dose ($TCID_{50}$), an amount of virus yielding 50% infection under defined conditions. A method for $TCID_{50}$ determination is detailed in Example 1 below. When cytopathology is noted in >90% of the cells, the infected cells and extracellular fluids (both of which contain viruses) are harvested as a single virus-cell lysate.

The highly concentrated virus stock to be used as a vaccine may be stored frozen (−50° C. or colder) or lyophilized until the time of use. Compounds such as NZ-amine, dextrose, gelatin or others designed to stabilize the virus during freezing and lyophilization may be added. The virus initially present in the virus-cell lysate may be further concentrated using commercially available equipment.

Typically, the concentration of virus in the vaccine formulation will be a minimum of $10^{6.5}$ $TCID_{50}$ per dose, but will typically be in the range of $10^{7.0}$ to $10^{9.0}$ $TCID_{50}$ per dose. At the time of vaccination, the virus is thawed (if frozen) or, if lyophilized, is reconstituted with a physiologically-acceptable carrier such as deionized water, saline, phosphate buffered saline, or the like.

The present invention is not limited to native (i.e. replication-competent) RRPVs. The virus-cell lysate can be subjected to treatments commonly used in the art to inactivate viruses. A composition comprising inactivated virus and expressed protein will be effective in eliciting protective immunity against FIPV if it contains a sufficient quantity of FIPV protein. This type of vaccine would provide added assurance that recipient felines will not be exposed to infectious FIPV as a consequence of vaccination. In addition, a physiologically-acceptable adjuvant may be added to the virus, such as EMA 31 (Ethylene Maleic anhydride 31) (Monsanto Co., St. Louis, Mo.), NEOCRYL (Polyvinyl Chemical Industries, Wilmington, Mass.), MVP (Modern Veterinary Products, Omaha, Nebr.), Squalene, PLURONIC L121 (polyoxypropylene-polyoxyethylene block copolymer) or the like.

Individual raccoon poxviruses expressing the N or E1 genes may be mixed together for vaccination. Furthermore, the virus may be mixed with additional inactivated or attenuated viruses, bacteria, or fungi such as feline leukemia virus, feline panleukopenia virus, feline rhinotracheitis virus, feline calicivirus, feline immunodeficiency virus, feline herpesvirus, feline enteric coronavirus, feline *Chlamydia psittaci*, *Microsporum canis*, or others. In addition, antigens from the above-cited organisms may be incorporated into combination vaccines. These antigens may be purified from natural sources or from recombinant expression systems, or may comprise individual subunits of the antigen or synthetic peptides derived therefrom.

In a further embodiment of the present invention, live or inactivated RRPV virus-cell lysates can be incorporated into liposomes, or encapsulated in peptide-, protein-, or polysaccharide-based microcapsules prior to administration, using means that are known in the art.

The final vaccine is administered to cats in a volume that may range from about 0.5 to about 5 ml. The vaccine can be administered by subcutaneous, intramuscular, oral intradermal, or intranasal routes. The number of injections and their temporal spacing may be varied. One to three vaccinations administered at intervals of one to three weeks are usually effective.

The following examples are intended to further illustrate the invention without limiting its scope. The techniques used to infect and transfect cells, plaque purify virus, perform immunoblot analysis are widely practiced in the art.

EXAMPLE 1

GENERATION OF RECOMBINANT RACCOON POX VIRUSES EXPRESSING FIPV N AND E1 GENES

1. Cloning of FIPV N and E1 Genes and Preparation of Transfer Plasmids

Figure 3B:
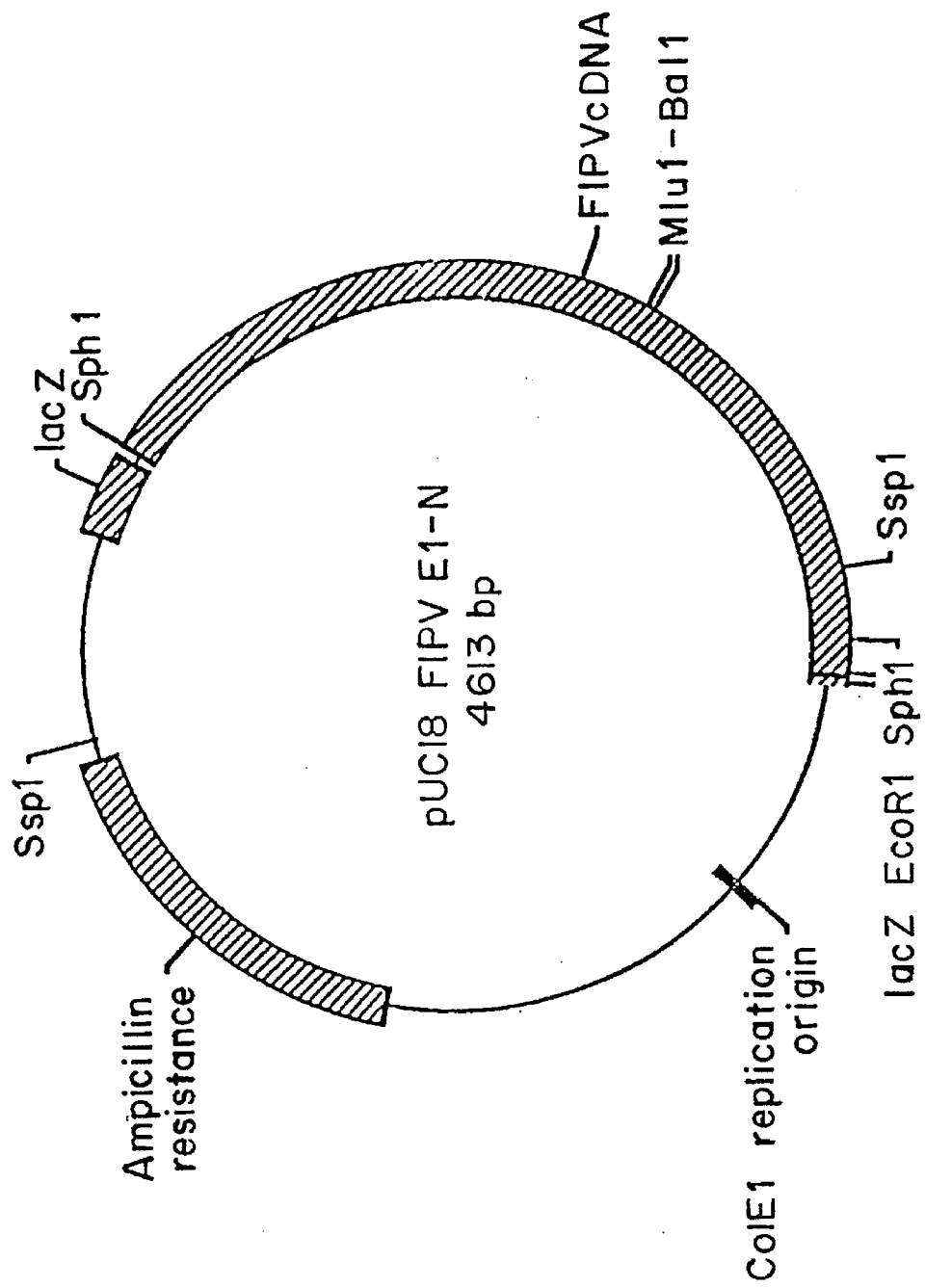
Figure 4A:
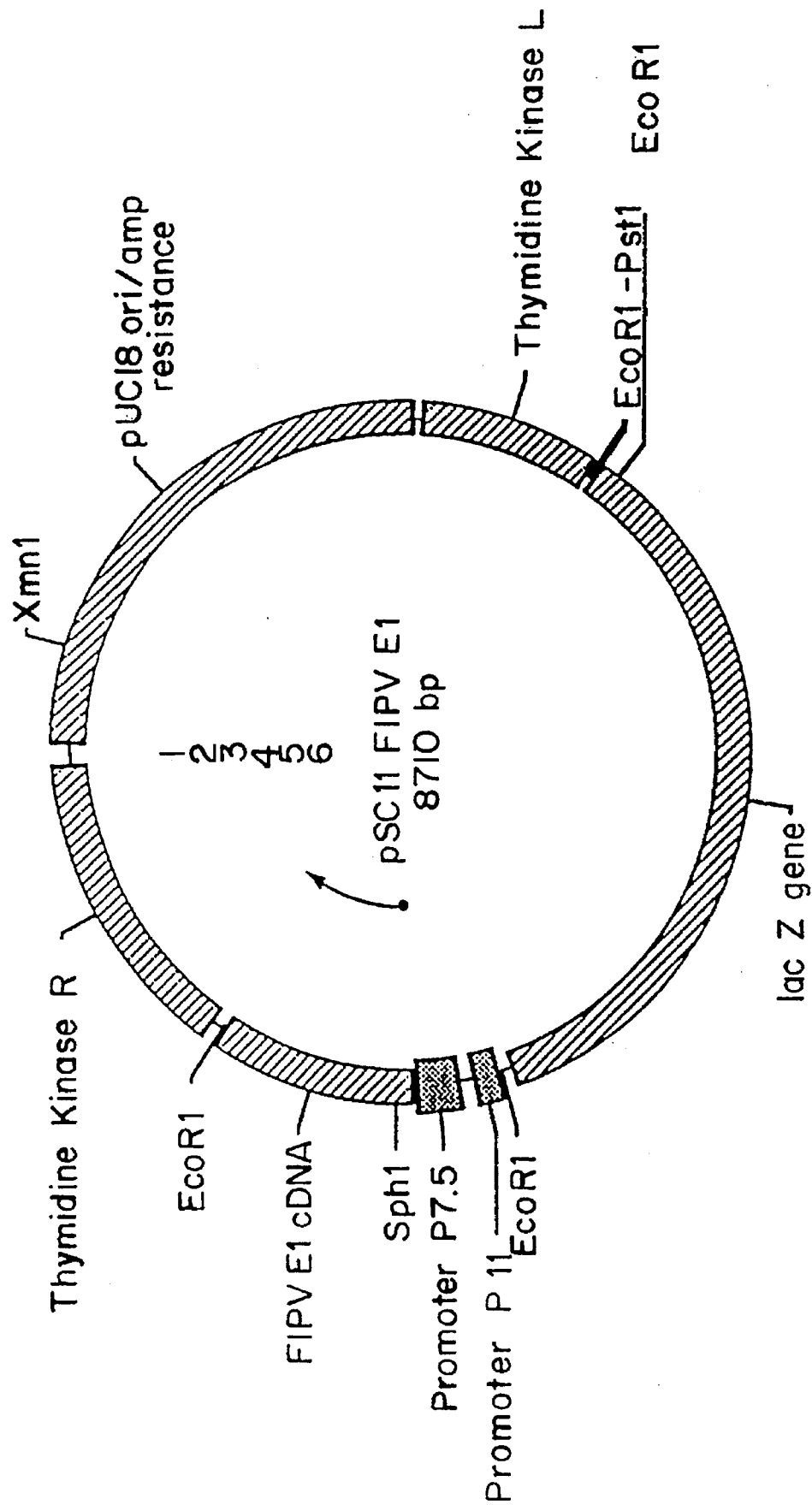
FIGS. 4A schematically shows the pSC11 transfer plasmid used to create RRPVs encoding the FIPV E1 protein.
Figure 4B:
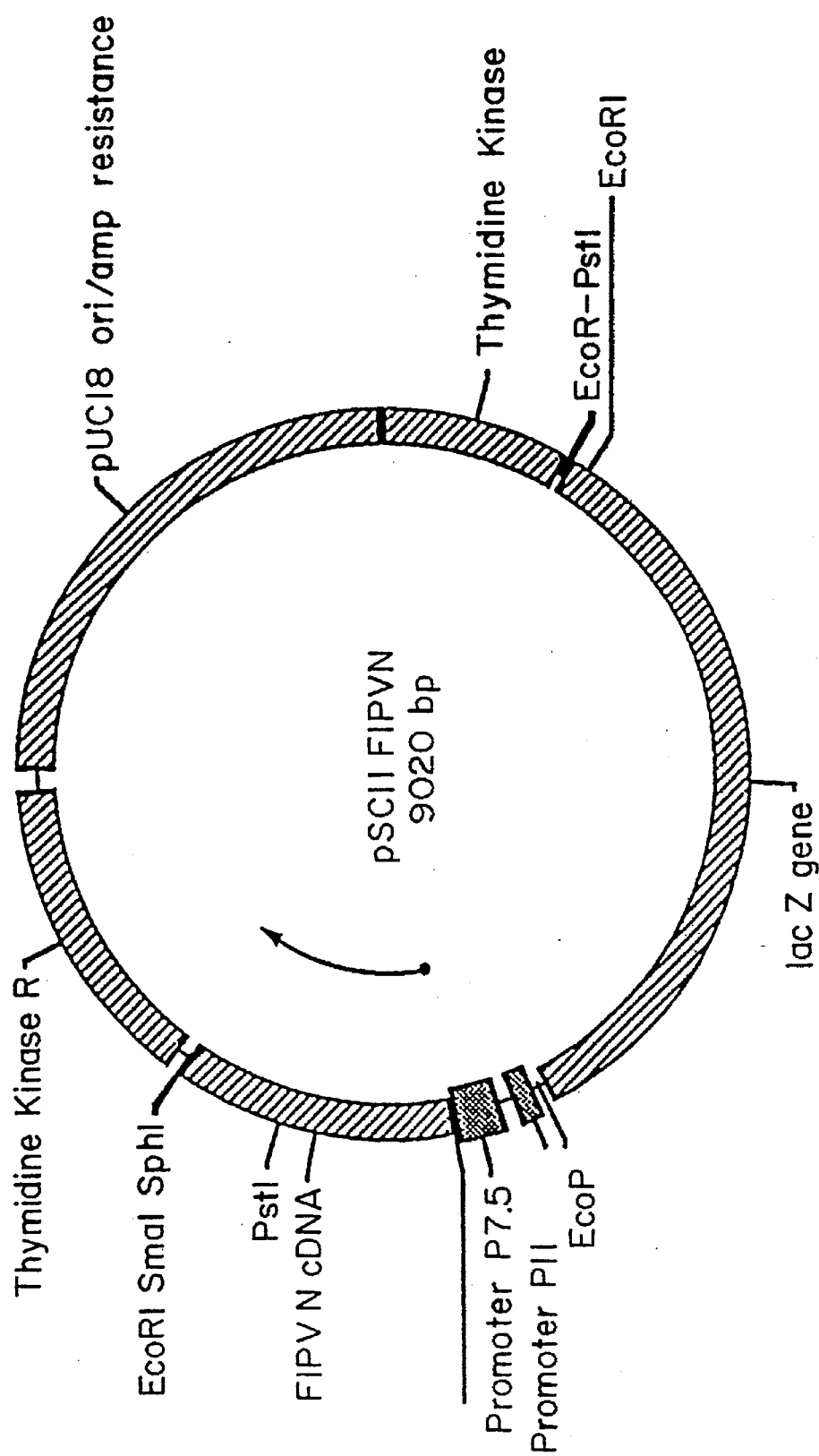
FIGS. 4B schematically shows the pSC11 transfer plasmid used to create RRPVs encoding the N protein.

The sequences of the E1 SEQ. ID. NO. 1 and N SEQ. ID. NO. 2 genes used in the present invention are shown in FIGS. 1A to 1E and 2A to 2G, respectively, of the specification. The methods for cloning of the N and E1 genes of FIPV and their insertion into a pSC11 transfer vector are detailed in European Patent Application 0,376,744, which is incorporated by reference. The plasmid used to clone the cDNA for the E1 and N genes is shown in FIGS. 3A and 3B. The pSC11 plasmids carrying the E1 and N genes are shown in FIGS. 4B and 4 B, respectively. The sequences of these plasmids are shown in FIGS. 5A to 5F (SEQ ID NO: 3) and FIGS. 6A to 6F (SEQ ID NO: 4).

To construct a pSC11 transfer plasmid containing both N and E1 genes, a 1.0 kb DNA fragment containing the vaccinia 7.5 promoter and the E1 gene was inserted downstream of the N gene in pSC11-FIPV N. The resulting plasmid was designated pSC11-FIPV N/E1.

2. Preparation of Recombinant Raccoon Poxviruses (RRPVs)

Monolayers of Vero cells (ATCC CCL 81) that were 80% confluent (approximately $5 \times 10^6$ cells/100 mm tissue culture dish) were infected for 30–60 minutes at 37° C. with wild-type raccoon pox virus (ATCC VR-338) at a multiplicity of infection MOI) of 0.1 $TCID_{50}$/cell. The medium (2 ml) consisted of Eagle's Minimum Essential Medium ("MEM", Gibco BRL #410–1500) containing 0.05% lactalbumin hydrolysate and 15 µg/ml gentamicin sulfate and adjusted to pH 7.2 with sodium bicarbonate. After infection, the medium was removed and the cells were transfected with the pSC11-FIPV N, pSC11-FIPV E1, or pSC11 N/E1 transfer plasmid by cationic liposome-mediated transfection using Dioctadecylamidoglycyclsperimine-4-trifluoroacetic acid, (TRANSFECTAM) (Promega Corporation, Madison, Wis.) and dioleoyloxy)propyl-N,N,N-trimethylammonium methyl sulfate (DOTAP) (Boehringer Mannheim, Indianapolis, Ind.), respectively, per manufacturer's instructions. The cells were incubated with the DNA-liposomes mixture in 3 ml of MEM containing 5% fetal bovine serum (FBS) overnight at 37° C. (5% $CO_2$), after which the medium was replaced with 8 ml of fresh MEM-5% FBS. The transfected cells were incubated at 37° C. (5% $CO_2$) until greater than 80% showed cytopathic effects (CPE), which took approximately 3–4 days. The virus-cell lysates were then removed from the plates and subjected to two cycles of freeze-thawing before storage at –70° C.

3. Isolation of Recombinant Raccoon Pox Virus Carrying the FIPV N Gene

RRPVs carrying the FIPV N gene (RRPV-FIPV N) were isolated and purified from the pSC11 -FIPV N Vero cell transfection by standard viral plaque purification methods. Monolayers of Vero cells (50–80% confluent) were infected with 2 ml of ten-fold serial dilutions ($10^{-1}$ to $10^{-3}$) of the viral-cell lysates for 1 hour at 37° C. After incubation, the media was removed and the infected cells were overlaid with 8–10 ml of 1.25% Noble agar containing MEM/5% FBS. The infected cells were then incubated for 3–4 days at 37° C. (5% $CO_2$), and overlaid again with 4 ml of 1.25% Nobel agar containing 0.5 X PBS and 600 µg/ml 5-bromo-4-chloro-3-indolyl-β-D-galactopyranoside (X-gal, States Biochemical Cleveland, Ohio). The plates were incubated at 37° C. (5% $CO_2$) for 4–16 hours, until blue (i.e. β-galactosidase positive) viral plaques were observed. The recombinant viral plaques were picked with sterile blunt needles attached to a 1 cc syringe, suspended in 0.5 ml of 0.25 µg/ml trypsin, vortexed vigorously, and incubated at 37° C. for 15–30 min. The disrupted viral plaques were then inoculated onto $5 \times 10^5$ Vero cells in 25 $cm^2$ flasks and incubated at 37° C. (5% $CO_2$) until greater than 80% CPE was observed. The viral-cell lysates containing RRPV-FIPV N were subjected to two cycles of freeze-thawing and stored at –70° C. Six individual RRPV-FIPV N clones were selected and plaque-purified five times as described above. Isolation of Recombinant Raccoon Pox Virus Containing the FIPV E1 Gene RRPVs carrying the FIPV E1 gene (RRPV-FIPV E1) were isolated and purified from pSC11-FIPV E1-transfected Vero cells using the methods described for rRPV-FIPV N, with some modifications. In this case, thymidine kinase deficient (tk-) RRPVs from the initial virus-cell lysates were selected on tk-RAT-2 cells (ATCC CRL 1764). This was performed by inoculating 1 ml of the initial virus-cell lysate onto a monolayer of RAT-2 cells in a 75 $cm^2$ flask (approximately $5 \times 10^6$ cells) in the presence of 5-bromodeoxyuridine (BrdU) at 30 µg/ml in MEM. The infected monolayer was incubated at 37° C. (5% $CO_2$) for 3–4 days until greater than 70% CPE was observed. The tk-virus-cell lysates were subjected to two cycles of freeze-thawing before storage at –70° C. Two individual RRPV-FIPV E1 clones were selected and subjected to six cycles of plaque purification as described above for RRPV-FIPV N.

5. Confirmation of FIPV N and E1 Genes in RRPV by Polymerase Chain Reaction

The presence of the FIPV N and E1 genes in the RRPVs was confirmed using the polymerase chain reaction (PCR). 90 µl of a virus-cell lysate were incubated with 10 µl of tenfold concentrated PCR lysis buffer (100 mM Tris-HCL buffer, pH 8.5; 500 mM KCl; 25 mM $MgCl_2$; 5% Tween 20 (polyoxyethylenesorbitan monolaurate); 3 mg/ml Proteinase K) for 16 hours at 50° C., then boiled for 10 min. 10 µl of this lysate was used in the PCR. PCR was performed in 100 µl of 10 mM Tris-HCL buffer, pH 8.3; 50 mM KCl; 200 uM of each deoxyribonucleotide triphosphate, 1.5 mM $MgCl_2$; 30 pmoles of each oligonucleotide primer; and 2.5 units of AMPLITAQ DNA polymerase (Taq DNA polymerase) (Perkin-Elmer Cetus, Norwalk, Conn.). The primers used in the PCR for FIPV N were:

5'-CTCGTGGTCGGAAGAATAATGATA-3'(SEQ ID NO: 7)   (1)

5'-AGCACCATAGAAAGTTGTCACATC-3'(SEQ ID NO: 8),  (2)

corresponding to nucleotides 68–91 and 721–744 of the FIPV N open reading frame (SEQ ID NO: 2) (primers 1 and 2, respectively). The primers used in the PCR for FIPV E1 were:

5'-TATGTAATGTTCGGCTTTAGTG-3'(SEQ ID NO: 9)    (3)

5'-GTGCTTCTGTTGAGTAATCACC-3'(SEQ ID NO: 10)   (4)

corresponding to nucleotides 334–355 and 721–742 of the FIPV E1 open reading frame SEQ. ID. NO. 1 (primers 3 and 4, respectively). The PCR amplifications were performed in a DNA Thermal Cycler Perkin-Elmer Cetus) by first heating the reaction mixes to 94° C. for denaturation, and then performing 35 cycles of amplification, each consisting of 1 min at 95° C., 1 min at 55° C., 2 min at 72° C., and, on the last cycle, a final incubation of 8 min at 72° C. 10 µl of the PCR products were resolved by electrophoresis in a horizontal-submarine 4% NUSIEVE (agarose) gel (FMC BioProducts, Rockland, Me.) in TAE buffer (40 mM Tris base, 20 mM sodium acetate, 1 mM EDTA, pH 7.2) by applying 5 V/cm for 1–2 hours. The DNA products were visualized by staining the gels with ethidium bromide.

Figure 7:
FIG. 7 is a photograph of an ethidium bromide-stained agarose gel showing the analysis of RRPV-FIPV N and RRPV-FIPV E1 by polymerase chain reaction.

PCR amplifications with the FIPV N and E1 primers gave DNA fragments of 676 and 408 nucleotides, respectively (FIG. 7). PCR amplifications using the pSC11 FIPV N and E1 transfer plasmids served as positive controls, and showed products of the predicted sizes. PCR amplifications using wild-type raccoon pox virus-Vero cell lysates served as a negative control, and no PCR products were observed in those samples.

Confirmation of RRPV FIPV N and E1 Protein Expression by Immunoblot Analysis

Confluent monolayers of Vero cells in a 25 $cm^2$ flask ($1–2 \times 10^6$ cells) were infected with clones of either RRPV- FIPV N or RRPV-FIPV E1 at an MOI of 0.1. The infected cell were incubated at 37° C. (5% $CO_2$) for 2–3 days until approximately 80% of the cells showed cytopathic effects. A virus-cell lysate was prepared, and 20 μl of the sample were added to 5 μl of 5 X Laemmli sample buffer (0.3M Tris-HCI buffer, pH 6.8, containing 5% SDS, 50% glycerol, 0.4% bromophenol blue, and 3% 2-β-mercaptoethanol) and heated at 95° C. for 5 min. The denatured protein samples were separated By SDS/polyacrylamide electrophoresis using a 4–15% gradient polyacrylamide gel as described previously. Maniatis et al., Molecular Cloning: A Laboratory Manual, 1982, Cold Spring Harbor Press. After electrophoresis, the proteins were transferred to nitrocellulose (Bio-Rad Laboratories, Hercules, Calif.) by electrotransfer using a Bio-Rad transfer apparatus per manufacturer's instructions. The transfer was performed in 25 mM Tris-HCI buffer, containing 0.2M glycine and 20% methanol, for 45 minutes at 50 V with constant current.

Figure 8:
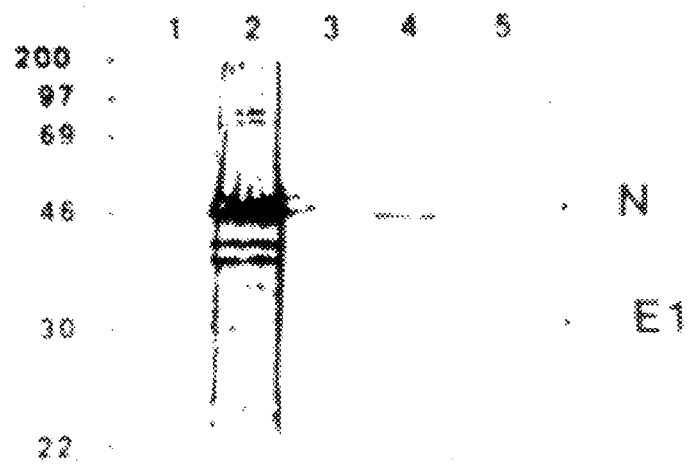
FIG. 8 is an imunoblot illustrating the detection of FIPV N and E1 proteins in virally infected cell lysates.

FIPV N and E1 proteins were visualized on the nitrocellulose filter using specific antibodies. Davis et al., Basic Methods in Molecular Biology, 1986, Elsevier Science Publishing Company, New York, N.Y. The filter was rinsed in phosphate buffered saline pH 7.4 containing 0.1% Tween-20 (polyoxyethylenesorbitan monolaurate) ("PBS-TW"), after which non-specific sites were blocked by overnight incubation at 4° C. in PBS containing 1% bovine serum albumin (PBS-BSA) followed by a 15 min wash in PBS-TW. The filter was then incubated for 30 min at room temperature with anti-FIPV antibodies, which consisted of ascites fluid from a FIPV (strain 79–1146)-infected cat, diluted 1:100 in PBS-TW containing 1% BSA ("PBS-TW-BSA"). After four 5 min washes in PBS-TW, the filter was incubated for 30 min at room temperature with a secondary antibody consisting of biotin-labeled mouse anti-cat IgG antibody (Kirkegaard & Perry Laboratories Inc., Gaithersburg, Md.) that had been diluted 1:2000 in PBS-TW-BSA, followed by four 5 min washes in PBS-TW. The filter was then incubated for 30 min at room temperature with horseradish peroxidase-conjugated streptavidin (Kirkegaard a Perry Laboratories Inc.) that had been diluted 1:1000 in PBS-TW. After the filter was washed four times (5 min each) in PBS-TW, the antigen-antibody complexes were visualized with peroxidase chromogenic substrate (Kirkegaard & Perry Laboratories Inc.). Sucrose-gradient purified FIPV and wild-type raccoon pox virus-Vero cell lysates were used as the positive and negative controls, respectively. A typical immunoblot is shown in FIG. 8.

7. Raccoon Poxvirus Titration

Serial tenfold dilutions of virus are prepared in MEM and inoculated in replicates of five onto Vero cells ($1\times10^4$ cells per well) in a 96 well plate. Virus preparations may be pretreated by dilution into an equal volume of 0.5% trypsin and incubation at 37° C. for 30 min in order to release virus from inclusions. Plates are incubated for 3–5 days at 37° C. (5% $CO_2$) and observed for cytopathology typical of raccoon poxvirus. Titers are calculated as 50% endpoints based on cytopathology using the methods of Reed and Muench, The American Journal of Hygiene 27(3):493–497) (1938).

EXAMPLE 2

PREPARATION OF VACCINE AND TESTING FOR EFFICACY IN CATS

1. Preparation of Master Seeds of RRPV-FIPV N and E1 Viruses

A single clone of each recombinant virus was selected for large-scale expansion to serve as a master seed virus. The criteria for selection were: 1) Demonstration of purity. Polymerase chain reaction was utilized to insure that the clone was uncontaminated with wild type virus. 2) Demonstration of adequate recombinant proten expression by Western blot or other antigen detection methods.

All recombinant virus expansions and titrations were done on Vero cells in MEM containing 2.5% FBS. Each plaque purified virus clone was expanded by inoculating a confluent monolayer of Vero cells in a 150 cm² flask ($1\times10^7$ cells) with 1 ml of viral-cell lysate (approximately $10^7$ infectious virus particles), and incubating at 37° C. (5% $CO_2$) until 100% cytopathic effect was observed (2–3 days). This virus-cell lysate was titrated on Vero cells as described in Example 1, and served as a premaster seed virus stock to obtain the master seed virus. The MOI to be used to produce the highest titer master seed virus was determined by inoculating a confluent monolayer of Vero cells in a roller bottle ($1\times10^8$ cells) with various MOIs of recombinant virus (e.g. 0.1, 0.05, 0.01, 0.005, and 0.001 $TCID_{50}$/cell.) The infected cells were incubated at 37° C. until greater than 80% CPE was observed (approximately 3 days), and the titers of each infected roller bottle was determined. The master seed viruses were aliquoted into 1.5 ml ampules, which were sealed and stored in a liquid nitrogen freezer.

2. Preparation of Vaccines $3\times10^7$ Vero cells were seeded into 850 cm² roller bottles in 200 ml of growth media (MEM containing 0.5% lactalbumin hydrolysate and 5% FBS) and incubated for 18 hours at 37° C. The next day, the medium was removed from the cells and replaced with 50ml of RRPV-FIPV N virus diluted to an MOI of 0.01 in infection media (MEM containing 0.5% lactalbumin hydrolysate and 2.5% FBS). The virus used was at the second passage beyond the master seed preparation. Virus was allowed to absorb to the cells for 30 min at 37° C., after which the volume of medium was adjusted to 150 ml per roller bottle. Roller bottles were incubated at 37° C. until 100% cytopathology was evident (3 days). The virus-cell lysate was harvested and stored frozen (−70° C.). The virus titer was determined to be $10^{6.97}$ TCID/ml.

RRPV-FIPV E1 stocks were prepared in the same manner, except that an MOI of 0.1 was used. The final virus preparation was titered and found to contain $10^{6.5}$ $TCID_{50}$/ml. Wild type raccoon poxvirus was grown using the same methods as described above, and contained $10^{6.44}$ $TCID_{50}$/ml.

3. Vaccination

A group of twenty-four 9-month-old cats (specific pathogen-free, Harlan Sprague Dawley, Madison, Wis.), comprising seven males and seventeen females, was used to demonstrate the efficacy of the RRPV-FIPV N vaccine. Cats were divided into five groups and vaccinated twice, 21 days apart, as indicated below:

| Group | # Cats | Vaccine | Volume (ml) | Viral Dose ($TCID_{50}$) | Vaccinaton Route* |
|---|---|---|---|---|---|
| 1 | 5 | RRPV-FIPV N | 3 | $10^{7.44}$ | SC |
| 2 | 5 | RRPV-FIPV N | 1 | $10^{6.97}$ | IM |
| 3 | 5 | RRPV-FIPV N | 3 | $10^{7.44}$ | ORAL |
| 4 | 4 | RRPV-FIPV N (1:10 Dilution) | 3 | $10^{6.44}$ | SC |
| 5 | 5 | Wild Type REV | 3 | $10^{6.44}$ | SC |

*SC = Subcutaneous
IM = Intramuscular
Oral = Oral

4. Challenge

Two weeks following the second vaccination, cats were orally inoculated with $10^{3.4}$ $TCID_{50}$ of Feline Enteric Coronavirus (strain 79–1683, ATCC VR-989). This virus induces a subclinical infection which can enhance subsequent FIPV infection. Three weeks later, cats were orally challenged with $10^{3.4}$ $TCID_{50}$ of FIPV (strain 79–1146, ATCC VR-990). Cats were monitored weekly for a total of 64 days after challenge for signs of clinical disease including: fever, icterus, leukopenia, anemia, weight loss, anorexia, depression, dehydration, and peritoneal swelling. Cats deemed moribund were euthanized by the attending veterinarian and post-mortem pathological examination was performed. Clinical disease signs were scored as follows:

| SIGN | SCORE |
|---|---|
| Fever | |
| 103.0–10.39° F. | 1 point/day* |
| 104.0–104.9° F. | 2 points/day |
| ≧105.0° F. | 3 points/day |
| Dehydration | 1 point/day |
| Depression | 1 point/day |
| Anorexia | 1 point/day |
| Peritoneal Swelling | 1 point/day |
| Icterus | 1 point/day |
| Weight Loss | |
| >20% | 1 point per observation |
| >30% | 2 points per observation |
| >50% | 5 points per observation |
| Leukopenia | |
| decrease of 50% | 3 points per observation |
| counts <6000 | 2 points per observation |
| Hematocrit <25% PCV | 3 points per observation |
| Death | 25 points |

*For cats with baseline temperatures averaging 103° F., no points will be scored until temperatures are in excess of 1° F. above baseline.

5. Evaluation of Induced Immunity to FIPV

Inoculation with virulent FIPV induced a fatal infection in 4/5 (80%) of the control cats, which were vaccinated with wild type raccoon poxvirus (Table 1). Both effusive and non-effusive forms of the disease were noted in the control cats. On the other hand, clinical disease was essentially absent after challenge of the subcutaneous vaccinates. The sporadic fever in these cats could be attributed to excitability and the slight anemia on one day in cat 1264 is not a significant finding. The subcutaneous vaccinates showed a statistically significant reduction in clinical signs ($p<0.05$, by ANOVA) and death ($p<0.01$, by Chi Square Analysis) when compared to the control cats.

The intramuscular route of vaccination was less effective in that 2/5 (40%) of the cats succumbed to FIPV-induced disease. However, the onset of disease in these cats was delayed when compared to the controls. The decreased efficacy may be related to the lower titer of virus inoculated into these cats because only a 1 ml dose could be administered by this route. There was also decreased efficacy when cats were inoculated by the oral route (60% mortality) which may indicate the need for a higher virus dose when vaccinated by this route.

The protection conferred against FIPV-caused disease by the subcutaneously administered vaccine was shown to be dose-dependent, confirming the benefit of a high-titer RRPV-FIPV vaccine in inducing protection against clinical disease induced by FIPV virus. A suitable vaccine dose contains viral antigen in the range of $10^4$–$10^8$ $TCID_{50}$/ml, preferably $10^7$–$10^8$ $TCID_{50}$/ml. A typical dose for administration to cats is 1–3 ml, and delivery by the subcutaneous route is preferred.

TABLE 1

TOTAL CLINICAL SCORES FOLLOWING CHALLENGE WITH FIPV

| CAT ID | Fever | Weight Loss | Leukopenia | Anemia | Chemical Signs | Death* | Total Score |
|---|---|---|---|---|---|---|---|
| SUBCUTANEOUS VACCINATES | | | | | | | |
| 1260 | 0 | 0 | 0 | 0 | 0 | 0 | 0 |
| 1262 | 1 | 0 | 0 | 0 | 0 | 0 | 1 |
| 1264 | 1 | 0 | 0 | 0 | 0 | 0 | 4 |
| 1266 | 0 | 0 | 0 | 0 | 0 | 0 | 0 |
| 1268 | 2 | 0 | 0 | 0 | 0 | 0 | 2 |
| INTRAMUSCULUAR VACCINATES | | | | | | | |
| 1270 | 13 | 6 | 0 | 0 | 33 | 25 | 77 |
| 1272 | 2 | 0 | 0 | 0 | 0 | 0 | 2 |
| 1297 | 23 | 0 | 0 | 0 | 34 | 25 | 91 |
| 1301 | 3 | 0 | 0 | 0 | 0 | 0 | 3 |
| ORAL VACCINATES | | | | | | | |
| 1303 | 1 | 0 | 4 | 0 | 0 | 0 | 5 |
| 1305 | 0 | 1 | 0 | 0 | 5 | 0 | 6 |
| 1307 | 3 | 1 | 0 | 0 | 4 | 25 | 33 |
| 1309 | 2 | 1 | 6 | 0 | 6 | 25 | 40 |
| 1311 | 4 | 3 | 0 | 0 | 18 | 25 | 50 |
| 1/10 DOSE SUBCUTANEOUS VACCINATES | | | | | | | |
| 1313 | 29 | 5 | 9 | 3 | 36 | 25 | 107 |
| 1315 | 17 | 0 | 0 | 0 | 20 | 25 | 62 |
| 1317 | 3 | 0 | 3 | 0 | 9 | 25 | 40 |
| 1319 | 1 | 0 | 0 | 0 | 6 | 0 | 7 |
| CONTROLS | | | | | | | |
| 1321 | 39 | 3 | 18 | 3 | 63 | 25 | 151 |
| 1323 | 5 | 0 | 2 | 0 | 14 | 25 | 46 |
| 1327 | 0 | 1 | 2 | 0 | 15 | 25 | 43 |
| 1329 | 5 | 1 | 6 | 0 | 11 | 25 | 48 |
| 1337 | 1 | 0 | 0 | 0 | 0 | 0 | 1 |

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 789 base pairs
        ( B ) TYPE: nucleic acid
        ( C ) STRANDEDNESS: double
        ( D ) TOPOLOGY: linear ( i i ) MOLECULE TYPE: cDNA ( v i ) ORIGINAL SOURCE:
        ( A ) ORGANISM: Feline infectious peritonitis virus ( v i i ) IMMEDIATE SOURCE:
        ( B ) CLONE: FIPV E1

( x i ) SEQUENCE DESCRIPTION: SEQ ID NO:1:

```
ATGAAGTACA TTTTGCTAAT ACTCGCGTGC ATAATTGCAT GCGTTTATGG TGAACGCTAC      60
TGTGCCATGC AAGACAGTGG CTTGCAGTGT ATTAATGGCA CAAATTCAAG ATGTCAAACC     120
TGCTTTGAAC GTGGTGATCT TATTTGGCAT CTTGCTAACT GGAACTTCAG CTGGTCTGTA     180
ATATTGATTG TTTTTATAAC AGTGTTACAA TATGGCAGAC CACAATTTAG CTGGCTCGTT     240
TATGGCATTA AAATGCTGAT CATGTGGCTA TTATGGCCTA TTGTTCTAGC GCTTACGATT     300
TTTAATGCAT ACTCTGAGTA CCAAGTTTCC AGATATGTAA TGTTCGGCTT TAGTGTTGCA     360
GGTGCAGTTG TAACGTTTGC ACTTTGGATG ATGTATTTTG TGAGATCTGT TCAGCTATAT     420
AGAAGAACCA AATCATGGTG GTCTTTTAAT CCTGAGACTA ATGCAATTCT TTGTGTTAAT     480
GCATTGGGTA GAAGTTATGT GCTTCCCTTA GATGGTACTC CTACAGGTGT TACCCTTACT     540
CTACTTTCAG GAAATCTATA TGCTGAAGGT TTCAAAATGG CTGGTGGTTT AACCATCGAG     600
CATTTGCCTA AATACGTCAT GATTGCTACA CCTAGTAGAA CCATCGTTTA TACATTAGTT     660
GGAAAACAAT TAAAAGCAAC TACTGCCACA GGATGGGCTT ACTACGTAAA ATCTAAAGCT     720
GGTGATTACT CAACAGAAGC ACGTACTGAC AATTTGAGTG AACATGAAAA ATTATTACAT     780
ATGGTGTAA                                                             789
```

( 2 ) INFORMATION FOR SEQ ID NO:2:

( i ) SEQUENCE CHARACTERISTICS:
        ( A ) LENGTH: 1134 base pairs
        ( B ) TYPE: nucleic acid
        ( C ) STRANDEDNESS: double
        ( D ) TOPOLOGY: linear ( i i ) MOLECULE TYPE: cDNA ( v i ) ORIGINAL SOURCE:
        ( A ) ORGANISM: Feline infectious peritonitis virus ( v i i ) IMMEDIATE SOURCE:
        ( B ) CLONE: FIPV N ( x i ) SEQUENCE DESCRIPTION: SEQ ID NO:2:

```
ATGGCCACAC AGGGACAACG CGTCAACTGG GGAGATGAAC CTTCCAAAAG ACGTGGTCGT      60
TCTAACTCTC GTGGTCGGAA GAATAATGAT ATACCTTTGT CATTCTACAA CCCCATTACC     120
CTCGAACAAG GATCTAAATT TTGGAATTTA TGTCCGAGAG ACCTTGTTCC CAAAGGAATA     180
GGTAATAAGG ATCAACAAAT TGGTTATTGG AATAGACAGA TTCGTTATCG TATTGTAAAA     240
```

| | | | | | | |
|---|---|---|---|---|---|---|
| GGCCAGCGTA | AGGAACTCGC | TGAGAGGTGG | TTCTTTTACT | TCTTAGGTAC | AGGACCTCAT | 300 |
| GCTGATGCTA | AATTCAAAGA | CAAGATTGAT | GGAGTCTTCT | GGGTTGCAAG | GGATGGTGCC | 360 |
| ATGAACAAGC | CCACAACGCT | TGGCACTCGT | GGAACCAATA | ACGAATCCAA | ACCACTGAGA | 420 |
| TTTGATGGTA | AGATACCGCC | ACAGTTTCAG | CTTGAAGTGA | ACCGTTCTAG | GAACAATTCA | 480 |
| AGGTCTGGTT | CTCAGTCTAG | ATCTGTTTCA | AGAAACAGAT | CTCAATCTAG | AGGAAGACAC | 540 |
| CATTCCAATA | ACCAGAATAA | TAATGTTGAG | GATACAATTG | TAGCCGTGCT | TGAAAAATTA | 600 |
| GGTGTTACTG | ACAAACAAAG | GTCACGTTCT | AAACCTAGAG | AACGTAGTGA | TTCCAAACCT | 660 |
| AGGGACACAA | CACCTAAGAA | TGCCAACAAA | CACACCTGGA | AGAAAACTGC | AGGCAAGGGA | 720 |
| GATGTGACAA | CTTTCTATGG | TGCTAGAAGT | AGTTCAGCTA | ACTTTGGTGA | TAGTGATCTC | 780 |
| GTTGCCAATG | GTAACGCTGC | CAAATGCTAC | CCTCAGATAG | CTGAATGTGT | TCCATCAGTG | 840 |
| TCTAGCATAA | TCTTTGGCAG | TCAATGGTCT | GCTGAAGAAG | CTGGTGATCA | AGTGAAAGTC | 900 |
| ACGCTCACTC | ACACCTACTA | CCTGCCAAAG | GATGATGCCA | AAACTAGTCA | ATTCCTAGAA | 960 |
| CAGATTGACG | CTTACAAGCG | ACCTTCTGAA | GTGGCTAAGG | ATCAGAGGCA | AAGAAGATCC | 1020 |
| CGTTCTAAGT | CTGCTGATAA | GAAGCCTGAG | GAGTTGTCTG | TAACTCTTGT | GGAGGCATAC | 1080 |
| ACAGATGTGT | TTGATGACAC | ACAGGTTGAG | ATGATTGATG | AGGTTACGAA | CTAA | 1134 |

( 2 ) INFORMATION FOR SEQ ID NO:3:

( i ) SEQUENCE CHARACTERISTICS:
        ( A ) LENGTH: 8710 base pairs
        ( B ) TYPE: nucleic acid
        ( C ) STRANDEDNESS: double
        ( D ) TOPOLOGY: circular ( i i ) MOLECULE TYPE: DNA (genomic)

( v i ) ORIGINAL SOURCE:
        ( A ) ORGANISM: Feline infectious peritonitis virus ( v i i ) IMMEDIATE SOURCE:
        ( B ) CLONE: psc11f1

( x i ) SEQUENCE DESCRIPTION: SEQ ID NO:3:

| | | | | | | |
|---|---|---|---|---|---|---|
| CGAAAGGGCC | TCGTGATACG | CCTATTTTTA | TAGGTTAATG | TCATGATAAT | AATGGTTTCT | 60 |
| TAGACGTCAG | GTGGCACTTT | TCGGGGAAAT | GTGCGCGGAA | CCCCTATTTG | TTTATTTTTC | 120 |
| TAAATACATT | CAAATATGTA | TCCGCTCATG | AGACAATAAC | CCTGATAAAT | GCTTCAATAA | 180 |
| TATTGAAAAA | GGAAGAGTAT | GAGTATTCAA | CATTTCCGTG | TCGCCCTTAT | TCCCTTTTTT | 240 |
| GCGGCATTTT | GCCTTCCTGT | TTTTGCTCAC | CCAGAAACGC | TGGTGAAAGT | AAAAGATGCT | 300 |
| GAAGATCAGT | TGGGTGCACG | AGTGGGTTAC | ATCGAACTGG | ATCTCAACAG | CGGTAAGATC | 360 |
| CTTGAGAGTT | TTCGCCCCGA | AGAACGTTTT | CCAATGATGA | GCACTTTTAA | AGTTCTGCTA | 420 |
| TGTGGCGCGG | TATTATCCCG | TATTGACGCC | GGGCAAGAGC | AACTCGGTCG | CCGCATACAC | 480 |
| TATTCTCAGA | ATGACTTGGT | TGAGTACTCA | CCAGTCACAG | AAAAGCATCT | TACGGATGGC | 540 |
| ATGACAGTAA | GAGAATTATG | CAGTGCTGCC | ATAACCATGA | GTGATAACAC | TGCGGCCAAC | 600 |
| TTACTTCTGA | CAACGATCGG | AGGACCGAAG | GAGCTAACCG | CTTTTTTGCA | CAACATGGGG | 660 |
| GATCATGTAA | CTCGCCTTGA | TCGTTGGGAA | CCGGAGCTGA | ATGAAGCCAT | ACCAAACGAC | 720 |
| GAGCGTGACA | CCACGATGCC | TGTAGCAATG | GCAACAACGT | TGCGCAAACT | ATTAACTGGC | 780 |
| GAACTACTTA | CTCTAGCTTC | CCGGCAACAA | TTAATAGACT | GGATGGAGGC | GGATAAAGTT | 840 |
| GCAGGACCAC | TTCTGCGCTC | GGCCCTTCCG | GCTGGCTGGT | TTATTGCTGA | TAAATCTGGA | 900 |

| | | | | | |
|---|---|---|---|---|---|
| GCCGGTGAGC | GTGGGTCTCG | CGGTATCATT | GCAGCACTGG | GGCCAGATGG | TAAGCCCTCC | 960 |
| CGTATCGTAG | TTATCTACAC | GACGGGGAGT | CAGGCAACTA | TGGATGAACG | AAATAGACAG | 1020 |
| ATCGCTGAGA | TAGGTGCCTC | ACTGATTAAG | CATTGGTAAC | TGTCAGACCA | AGTTTACTCA | 1080 |
| TATATACTTT | AGATTGATTT | AAAACTTCAT | TTTTAATTTA | AAAGGATCTA | GGTGAAGATC | 1140 |
| CTTTTTGATA | ATCTCATGAC | CAAATCCCT | TAACGTGAGT | TTTCGTTCCA | CTGAGCGTCA | 1200 |
| GACCCCGTAG | AAAAGATCAA | AGGATCTTCT | TGAGATCCTT | TTTTTCTGCG | CGTAATCTGC | 1260 |
| TGCTTGCAAA | CAAAAAAACC | ACCGCTACCA | GCGGTGGTTT | GTTTGCCGGA | TCAAGAGCTA | 1320 |
| CCAACTCTTT | TTCCGAAGGT | AACTGGCTTC | AGCAGAGCGC | AGATACCAAA | TACTGTCCTT | 1380 |
| CTAGTGTAGC | CGTAGTTAGG | CCACCACTTC | AAGAACTCTG | TAGCACCGCC | TACATACCTC | 1440 |
| GCTCTGCTAA | TCCTGTTACC | AGTGGCTGCT | GCCAGTGGCG | ATAAGTCGTG | TCTTACCGGG | 1500 |
| TTGGACTCAA | GACGATAGTT | ACCGGATAAG | GCGCAGCGGT | CGGGCTGAAC | GGGGGGTTCG | 1560 |
| TGCACACAGC | CCAGCTTGGA | GCGAACGACC | TACACCGAAC | TGAGATACCT | ACAGCGTGAG | 1620 |
| CATTGAGAAA | GCGCCACGCT | TCCCGAAGGG | AGAAAGGCGG | ACAGGTATCC | GGTAAGCGGC | 1680 |
| AGGGTCGGAA | CAGGAGAGCG | CACGAGGGAG | CTTCCAGGGG | GAAACGCCTG | GTATCTTTAT | 1740 |
| AGTCCTGTCG | GGTTTCGCCA | CCTCTGACTT | GAGCGTCGAT | TTTTGTGATG | CTCGTCAGGG | 1800 |
| GGGCGGAGCC | TATGGAAAAA | CGCCAGCAAC | GCGGCCTTTT | TACGGTTCCT | GGCCTTTTGC | 1860 |
| TGGCCTTTTG | CTCACATGTT | CTTTCCTGCG | TTATCCCCTG | ATTCTGTGGA | TAACCGTATT | 1920 |
| ACCGCCTTTG | AGTGAGCTGA | TACCGCTCGC | CGCAGCCGAA | CGACCGAGCG | CAGCGAGTCA | 1980 |
| GTGAGCGAGG | AAGCGGAAGA | GCGCCCAATA | CGCAAACCGC | CTCTCCCCGC | GCGTTGGCCG | 2040 |
| ATTCATTAAT | GCAGCTGGCA | CGACAGGTTT | CCCGACTGGA | AAGCGGGCAG | TGAGCGCAAC | 2100 |
| GCAATTAATG | TGAGTTAGCT | CACTCATTAG | GCACCCCAGG | CTTTACACTT | TATGCTTCCG | 2160 |
| GCTCGTATGT | TGTGTGGAAT | TGTGAGCGGA | TAACAATTTC | ACACAGGAAA | CAGCTATGAC | 2220 |
| CATGATTACG | CCAAGCTTTT | GCGATCAATA | AATGGATCAC | AACCAGTATC | TCTTAACGAT | 2280 |
| GTTCTTCGCA | GATGATGATT | CATTTTTTAA | GTATTGGCT | AGTCAAGATG | ATGAAATCTT | 2340 |
| CATTATCTGA | TATATTGCAA | ATCACTCAAT | ATCTAGACTT | TCTGTTATTA | TTATTGATCC | 2400 |
| AATCAAAAAA | TAAATTAGAA | GCCGTGGGTC | ATTGTTATGA | ATCTCTTTCA | GAGGAATACA | 2460 |
| GACAATTGAC | AAAATTCACA | GACTTTCAAG | ATTTTAAAAA | ACTGTTTAAC | AAGGTCCCTA | 2520 |
| TTGTTACAGA | TGGAAGGGTC | AAACTTAATA | AAGGATATTT | GTTCGACTTT | GTGATTAGTT | 2580 |
| TGATGCGATT | CAAAAAAGAA | TCCTCTCTAG | CTACCACCGC | AATAGATCCT | GTTAGATACA | 2640 |
| TAGATCCTCG | TCGCAATATC | GCATTTCTA | ACGTGATGGA | TATATTAAAG | TCGAATAAAG | 2700 |
| TGAACAATAA | TTAATTCTTT | ATTGTCATCA | TGAACGGCGG | ACATATTCAG | TTGATAATCG | 2760 |
| GCCCCATGTT | TTCAGGTAAA | AGTACAGAAT | TAATTAGACG | AGTTAGACGT | TATCAAATAG | 2820 |
| CTCAATATAA | ATGCGTGACT | ATAAAATATT | CTAACGATAA | TAGATACGGA | ACGGGACTAT | 2880 |
| GGACGCATGA | TAAGAATAAT | TTTGAAGCAT | TGGAAGCAAC | TAAACTATGT | GATCTCTTGG | 2940 |
| AATCAATTAC | AGATTTCTCC | GTGATAGGTA | TCGATGAAGG | ACAGTTCTTT | CCAGACATTG | 3000 |
| TTGAATTCCG | AGCTTGGCTG | CAGGTCGGGG | ATCCCCCTG | CCCGGTTATT | ATTATTTTTG | 3060 |
| ACACCAGACC | AACTGGTAAT | GGTAGCGAAC | GGCGCTCAGC | TGAATTCCGC | CGATACTGAC | 3120 |
| GGGCTCCAGG | AGTCGTCGCC | ACCAATCCCC | ATATGGAAAC | CGTCGATATT | CAGCCATGTG | 3180 |
| CCTTCTTCCG | CGTGCAGCAG | ATGGCGATGG | CTGGTTTCCA | TCAGTTGCTG | TTGACTGTAG | 3240 |
| CGGCTGATGT | TGAACTGGAA | GTCGCCGCGC | CACTGGTGTG | GGCCATAATT | CAATTCGCGC | 3300 |

```
GTCCCGCAGC  GCAGACCGTT  TTCGCTCGGG  AAGACGTACG  GGGTATACAT  GTCTGACAAT    3360

GGCAGATCCC  AGCGGTCAAA  ACAGGCGGCA  GTAAGGCGGT  CGGGATAGTT  TTCTTGCGGC    3420

CCTAATCCGA  GCCAGTTTAC  CCGCTCTGCT  ACCTGCGCCA  GCTGGCAGTT  CAGGCCAATC    3480

CGCGCCGGAT  GCGGTGTATC  GCTCGCCACT  TCAACATCAA  CGGTAATCGC  CATTTGACCA    3540

CTACCATCAA  TCCGGTAGGT  TTTCCGGCTG  ATAAATAAGG  TTTTCCCCTG  ATGCTGCCAC    3600

GCGTGACCGG  TCGTAATCAG  CACCGCATCA  GCAAGTGTAT  CTGCCGTGCA  CTGCAACAAC    3660

GCTGCTTCGG  CCTGGTAATG  GCCCGCCGCC  TTCCAGCGTT  CGACCCAGGC  GTTAGGGTCA    3720

ATGCGGGTCG  CTTCACTTAC  GCCAATGTCG  TTATCCAGCG  GTGCACGGGT  GAACTGATCG    3780

CGCAGCGGCG  TCAGCAGTTG  TTTTTTATCG  CCAATCCACA  TCTGTGAAAG  AAAGCCTGAC    3840

TGGCGGTTAA  ATTGCCAACG  CTTATTACCC  AGCTCGATGC  AAAAATCCAT  TTCGCTGGTG    3900

GTCAGATGCG  GGATGGCGTG  GGACGCGGCG  GGGAGCGTCA  CACTGAGGTT  TTCCGCCAGA    3960

CGCCACTGCT  GCCAGGCGCT  GATGTGCCCG  GCTTCTGACC  ATGCGGTCGC  GTTCGGTTGC    4020

ACTACGCGTA  CTGTGAGCCA  GAGTTGCCCG  GCGCTCTCCG  GCTGCGGTAG  TTCAGGCAGT    4080

TCAATCAACT  GTTTACCTTG  TGGAGCGACA  TCCAGAGGCA  CTTCACCGCT  TGCCAGCGGC    4140

TTACCATCCA  GCGCCACCAT  CCAGTGCAGG  AGTCGTTAT   CGCTATGACG  GAACAGGTAT    4200

TCGCTGGTCA  CTTCGATGGT  TTGCCCGGAT  AAACGGAACT  GGAAAAACTG  CTGCTGGTGT    4260

TTTGCTTCCG  TCAGCGCTGG  ATGCGGCGTG  CGGTCGGCAA  AGACCAGACC  GTTCATACAG    4320

AACTGGCGAT  CGTTCGGCGT  ATCGCCAAAA  TCACCGCCGT  AAGCCGACCA  CGGGTTGCCG    4380

TTTTCATCAT  ATTTAATCAG  CGACTGATCC  ACCCAGTCCC  AGACGAAGCC  GCCCTGTAAA    4440

CGGGGATACT  GACGAAACGC  CTGCCAGTAT  TTAGCGAAAC  CGCCAAGACT  GTTACCCATC    4500

GCGTGGGCGT  ATTCGCAAAG  GATCAGCGGG  CGCGTCTCTC  CAGGTAGCGA  AAGCCATTTT    4560

TTGATGGACC  ATTTCGGCAC  AGCCGGGAAG  GGCTGGTCTT  CATCCACGCG  CGCGTACATC    4620

GGGCAAATAA  TATCGGTGGC  CGTGGTGTCG  GCTCCGCCGC  CTTCATACTG  CACCGGGCGG    4680

GAAGGATCGA  CAGATTTGAT  CCAGCGATAC  AGCGCGTCGT  GATTAGCGCC  GTGGCCTGAT    4740

TCATTCCCCA  GCGACCAGAT  GATCACACTC  GGGTGATTAC  GATCGCGCTG  CACCATTCGC    4800

GTTACGCGTT  CGCTCATCGC  CGGTAGCCAG  CGCGGATCAT  CGGTCAGACG  ATTGATTGGC    4860

ACCATGCCGT  GGGTTTCAAT  ATTGGCTTCA  TCCACCACAT  ACAGGCCGTA  GCGGTCGCAC    4920

AGCGTGTACC  ACAGCGGATG  GTTCGGATAA  TGCGAACAGC  GCACGGCGTT  AAAGTTGTTC    4980

TGCTTCATCA  GCAGGATATC  CTGCACCATC  GTCTGCTCAT  CCATGACCTG  ACCATGCAGA    5040

GGATGATGCT  CGTGACGGTT  AACGCCTCGA  ATCAGCAACG  GCTTGCCGTT  CAGCAGCAGC    5100

AGACCATTTT  CAATCCGCAC  CTCGCGGAAA  CCGACATCGC  AGGCTTCTGC  TTCAATCAGC    5160

GTGCCGTCGG  CGGTGTGCAG  TTCAACCACC  GCACGATAGA  GATTCGGGAT  TTCGGCGCTC    5220

CACAGTTTCG  GGTTTTCGAC  CTTGAGACGT  AGTGTGACGC  GATCGGCATA  ACCACCACGC    5280

TCATCGATAA  TTTCACCGCC  GAAAGGCGCG  GTGCCGCTGG  CGACCTGCGT  TTCACCCTGC    5340

CATAAAGAAA  CTGTTACCCG  TAGGTAGTCA  CGCAACTCGC  CGCACATCTG  AACTTCAGCC    5400

TCCAGTACAG  CGCGGCTGAA  ATCATCATTA  AAGCGAGTGG  CAACATGGAA  ATCGCTGATT    5460

TGTGTAGTCG  GTTTATGCAG  CAACGAGACG  TCACGGAAAA  TGCCGCTCAT  CCGCCACATA    5520

TCCTGATCTT  CCAGATAACT  GCCGTCACTC  CAACGCAGCA  CCATCACCGC  GAGGCGGTTT    5580

TCTCCGGCGC  GTAAAATGC   GCTCAGGTCA  AATTCAGACG  GCAAACGACT  GTCCTGGCCG    5640

TAACCGACCC  AGCGCCCGTT  GCACCACAGA  TGAAACGCCG  AGTTAACGCC  ATCAAAAATA    5700
```

-continued

```
ATTCGCGTCT GGCCTTCCTG TAGCCAGCTT TCATCAACAT TAAATGTGAG CGAGTAACAA    5760
CCCGTCGGAT TCTCCGTGGG AACAAACGGC GGATTGACCG TAATGGGATA GGTTACGTTG    5820
GTGTAGATGG GCGCATCGTA ACCGTGCATC TGCCAGTTTG AGGGGACGAC GACAGTATCG    5880
GCCTCAGGAA GATCGCACTC CAGCCAGCTT TCCGGCACCG CTTCTGGTGC CGGAAACCAG    5940
GCAAAGCGCC ATTCGCCATT CAGGCTGCGC AACTGTTGGG AAGGGCGATC GGTGCGGGCC    6000
TCTTCGCTAT TACGCCAGCT GGCGAAAGGG GGATGTGCTG CAAGGCGATT AAGTTGGGTA    6060
ACGCCAGGGT TTTCCCAGTC ACGACGTTGT AAAACGACGG GATCCCTCGA GGAATTCATT    6120
TATAGCATAG AAAAAAACAA AATGAAATTC TACTATATTT TTACATACAT ATATTCTAAA    6180
TATGAAAGTG GTGATTGTGA CTAGCGTAGC ATCGCTTCTA GACATATACT ATATAGTAAT    6240
ACCAATACTC AAGACTACGA AACTGATACA ATCTCTTATC ATGTGGGTAA TGTTCTCGAT    6300
GTCGAATAGC CATATGCCGG TAGTTGCGAT ATACATAAAC TGATCACTAA TTCCAAACCC    6360
ACCGCTTTT TATAGTAAGT TTTTCACCCA TAAATAATAA ATACAATAAT TAATTTCTCG    6420
TAAAAGTAGA AAATATATTC TAATTTATTG CACGGTAAGG AAGTAGAATC ATAAAGAACA    6480
GTGACGGATC CCAATTCGGG CATTTTTGGT TTGAACTAAA CAAAATGAAG TACATTTTGC    6540
TAATACTCGC GTGCATAATT GCATGCGTTT ATGGTGAACG CTACTGTGCC ATGCAAGACA    6600
GTGGCTTGCA GTGTATTAAT GGCACAAATT CAAGATGTCA AACCTGCTTT GAACGTGGTG    6660
ATCTTATTTG GCATCTTGCT AACTGGAACT TCAGCTGGTC TGTAATATTG ATTGTTTTA    6720
TAACAGTGTT ACAATATGGC AGACCACAAT TTAGCTGGCT CGTTATGGC ATTAAAATGC    6780
TGATCATGTG GCTATTATGG CCTATTGTTC TAGCGCTTAC GATTTTAAT GCATACTCTG    6840
AGTACCAAGT TTCCAGATAT GTAATGTTCG GCTTAGTGT TGCAGGTGCA GTTGTAACGT    6900
TTGCACTTTG GATGATGTAT TTTGTGAGAT CTGTTCAGCT ATATAGAAGA ACCAAATCAT    6960
GGTGGTCTTT TAATCCTGAG ACTAATGCAA TTCTTTGTGT TAATGCATTG GGTAGAAGTT    7020
ATGTGCTTCC CTTAGATGGT ACTCCTACAG GTGTTACCCT TACTCTACTT TCAGGAAATC    7080
TATATGCTGA AGGTTTCAAA ATGGCTGGTG GTTAACCAT CGAGCATTTG CCTAAATACG    7140
TCATGATTGC TACACCTAGT AGAACCATCG TTTATACATT AGTTGGAAAA CAATTAAAAG    7200
CAACTACTGC CACAGGATGG GCTTACTACG TAAAATCTAA AGCTGGTGAT TACTCAACAG    7260
AAGCACGTAC TGACAATTTG AGTGAACATG AAAAATTATT ACATATGGTG TAACTAAACT    7320
TTCAAATGGG GGAATTCTGT GAGCGTATGG CAAACGAAGG AAAAATTAGT TATAGTAGCC    7380
GCACTCGATG GGACATTTCA ACGTAAACCG TTTAATAATA TTTGAATCT TATTCCATTA    7440
TCTGAAATGG TGGTAAAACT AACTGCTGTG TGTATGAAAT GCTTAAGGA GGCTTCCTTT    7500
TCTAAACGAT TGGGTGAGGA AACCGAGATA GAAATAATAG GAGGTAATGA TATGTATCAA    7560
TCGGTGTGTA GAAAGTGTTA CATCGACTCA TAATATTATA TTTTTATCT AAAAAACTAA    7620
AAATAAACAT TGATTAAATT TTAATATAAT ACTAAAAAT GGATGTTGTG TCGTTAGATA    7680
AACCGTTTAT GTATTTGAG GAAATTGATA ATGAGTTAGA TTACGAACCA GAAAGTGCAA    7740
ATGAGGTCGC AAAAAAACTG CCGTATCAAG GACAGTTAAA ACTATTACTA GGAGAATTAT    7800
TTTTTCTTAG TAAGTTACAG CGACACGGTA TATTAGATGG TGCCACCGTA GTGTATATAG    7860
GATCTGCTCC CGGTACACAT ATACGTTATT TGAGAGATCA TTTCTATAAT TTAGGAGTGA    7920
TCATCAAATG GATGCTAATT GACGGCCGCC ATCATGATCC TATTTAAAT GGATTGCGTG    7980
ATGTGACTCT AGTGACTCGG TTCGTTGATG AGGAATATCT ACGATCCATC AAAAAACAAC    8040
TGCATCCTTC TAAGATTATT TTAATTTCTG ATGTGAGATC CAAACGAGGA GGAAATGAAC    8100
```

```
CTAGTACGGC GGATTTACTA AGTAATTACG CTCTACAAAA TGTCATGATT AGTATTTTAA      8160

ACCCCGTGGC GTCTAGTCTT AAATGGAGAT GCCCGTTTCC AGATCAATGG ATCAAGGACT      8220

TTTATATCCC ACACGGTAAT AAAATGTTAC AACCTTTTGC TCCTTCATAT TCAGGGCCGT      8280

CGTTTTACAA CGTCGTGACT GGGAAAACCC TGGCGTTACC CAACTTAATC GCCTTGCAGC      8340

ACATCCCCCT TTCGCCAGCT GGCGTAATAG CGAAGAGGCC CGCACCGATC GCCCTTCCCA      8400

ACAGTTGCGC AGCCTGAATG GCGAATGGCG CCTGATGCGG TATTTTCTCT TACGCATCT      8460

GTGCGGTATT TCACACCGCA TATGGTGCAC TCTCAGTACC ATCTGCTCTG ATGCCGCATA      8520

GTTAAGCCAG TACACTCCGC TATCGCTACG TGACTGGGTC ATGGCTGCGC CCGACACCC      8580

GCCAACACCC GCTGACGCGC CCTGACGGGC TTGTCTGCTC CCGGCATCCG CTTACAGACA      8640

AGCTGTGACC GTCTCCGGGA GCTGCATGTG TCAGAGGTTT TCACCGTCAT CACCGAAACG      8700

CGCGAGGCAG                                                             8710
```

( 2 ) INFORMATION FOR SEQ ID NO:4:

( i ) SEQUENCE CHARACTERISTICS:
    ( A ) LENGTH: 9019 base pairs
    ( B ) TYPE: nucleic acid
    ( C ) STRANDEDNESS: double
    ( D ) TOPOLOGY: circular ( i i ) MOLECULE TYPE: DNA (genomic)

( v i ) ORIGINAL SOURCE:
    ( A ) ORGANISM: Feline immunodeficiency virus ( v i i ) IMMEDIATE SOURCE:
    ( B ) CLONE: psc11e1

( x i ) SEQUENCE DESCRIPTION: SEQ ID NO:4:

```
GAAAGGGCCT CGTGATACGC CTATTTTTAT AGGTTAATGT CATGATAATA ATGGTTTCTT       60

AGACGTCAGG TGGCACTTTT CGGGGAAATG TGCGCGGAAC CCCTATTTGT TTATTTTTCT      120

AAATACATTC AAATATGTAT CCGCTCATGA GACAATAACC CTGATAAATG CTTCAATAAT      180

ATTGAAAAAG GAAGAGTATG AGTATTCAAC ATTTCCGTGT CGCCCTTATT CCCTTTTTTG      240

CGGCATTTTG CCTTCCTGTT TTTGCTCACC CAGAAACGCT GGTGAAAGTA AAAGATGCTG      300

AAGATCAGTT GGGTGCACGA GTGGGTTACA TCGAACTGGA TCTCAACAGC GGTAAGATCC      360

TTGAGAGTTT TCGCCCCGAA GAACGTTTTC CAATGATGAG CACTTTTAAA GTTCTGCTAT      420

GTGGCGCGGT ATTATCCCGT ATTGACGCCG GGCAAGAGCA ACTCGGTCGC CGCATACACT      480

ATTCTCAGAA TGACTTGGTT GAGTACTCAC CAGTCACAGA AAAGCATCTT ACGGATGGCA      540

TGACAGTAAG AGAATTATGC AGTGCTGCCA TAACCATGAG TGATAACACT GCGGCCAACT      600

TACTTCTGAC AACGATCGGA GGACCGAAGG AGCTAACCGC TTTTTTGCAC AACATGGGGG      660

ATCATGTAAC TCGCCTTGAT CGTTGGGAAC CGGAGCTGAA TGAAGCCATA CCAAACGACG      720

AGCGTGACAC CACGATGCCT GTAGCAATGG CAACAACGTT GCGCAAACTA TTAACTGGCG      780

AACTACTTAC TCTAGCTTCC CGGCAACAAT TAATAGACTG GATGGAGGCG GATAAAGTTG      840

CAGGACCACT TCTGCGCTCG GCCCTTCCGG CTGGCTGGTT TATTGCTGAT AAATCTGGAG      900

CCGGTGAGCG TGGGTCTCGC GGTATCATTG CAGCACTGGG GCCAGATGGT AAGCCCTCCC      960

GTATCGTAGT TATCTACACG ACGGGGAGTC AGGCAACTAT GGATGAACGA AATAGACAGA     1020

TCGCTGAGAT AGGTGCCTCA CTGATTAAGC ATTGGTAACT GTCAGACCAA GTTTACTCAT     1080

ATATACTTTA GATTGATTTA AAACTTCATT TTTAATTTAA AAGGATCTAG GTGAAGATCC     1140

TTTTTGATAA TCTCATGACC AAAATCCCTT AACGTGAGTT TTCGTTCCAC TGAGCGTCAG     1200
```

```
ACCCCGTAGA  AAAGATCAAA  GGATCTTCTT  GAGATCCTTT  TTTTCTGCGC  GTAATCTGCT   1260
GCTTGCAAAC  AAAAAAACCA  CCGCTACCAG  CGGTGGTTTG  TTTGCCGGAT  CAAGAGCTAC   1320
CAACTCTTTT  TCCGAAGGTA  ACTGGCTTCA  GCAGAGCGCA  GATACCAAAT  ACTGTCCTTC   1380
TAGTGTAGCC  GTAGTTAGGC  CACCACTTCA  AGAACTCTGT  AGCACCGCCT  ACATACCTCG   1440
CTCTGCTAAT  CCTGTTACCA  GTGGCTGCTG  CCAGTGGCGA  TAAGTCGTGT  CTTACCGGGT   1500
TGGACTCAAG  ACGATAGTTA  CCGGATAAGG  CGCAGCGGTC  GGGCTGAACG  GGGGGTTCGT   1560
GCACACAGCC  CAGCTTGGAG  CGAACGACCT  ACACCGAACT  GAGATACCTA  CAGCGTGAGC   1620
ATTGAGAAAG  CGCCACGCTT  CCCGAAGGGA  GAAAGGCGGA  CAGGTATCCG  GTAAGCGGCA   1680
GGGTCGGAAC  AGGAGAGCGC  ACGAGGGAGC  TTCCAGGGGG  AAACGCCTGG  TATCTTTATA   1740
GTCCTGTCGG  GTTTCGCCAC  CTCTGACTTG  AGCGTCGATT  TTTGTGATGC  TCGTCAGGGG   1800
GGCGGAGCCT  ATGGAAAAAC  GCCAGCAACG  CGGCCTTTTT  ACGGTTCCTG  GCCTTTTGCT   1860
GGCCTTTTGC  TCACATGTTC  TTTCCTGCGT  TATCCCCTGA  TTCTGTGGAT  AACCGTATTA   1920
CCGCCTTTGA  GTGAGCTGAT  ACCGCTCGCC  GCAGCCGAAC  GACCGAGCGC  AGCGAGTCAG   1980
TGAGCGAGGA  AGCGGAAGAG  CGCCCAATAC  GCAAACCGCC  TCTCCCCGCG  CGTTGGCCGA   2040
TTCATTAATG  CAGCTGGCAC  GACAGGTTTC  CCGACTGGAA  AGCGGGCAGT  GAGCGCAACG   2100
CAATAATGT  GAGTTAGCTC  ACTCATTAGG  CACCCCAGGC  TTTACACTTT  ATGCTTCCGG   2160
CTCGTATGTT  GTGTGGAATT  GTGAGCGGAT  AACAATTTCA  CACAGGAAAC  AGCTATGACC   2220
ATGATTACGC  CAAGCTTTTG  CGATCAATAA  ATGGATCACA  ACCAGTATCT  CTTAACGATG   2280
TTCTTCGCAG  ATGATGATTC  ATTTTTTAAG  TATTTGGCTA  GTCAAGATGA  TGAAATCTTC   2340
ATTATCTGAT  ATATTGCAAA  TCACTCAATA  TCTAGACTTT  CTGTTATTAT  TATTGATCCA   2400
ATCAAAAAAT  AAATTAGAAG  CCGTGGGTCA  TTGTTATGAA  TCTCTTTCAG  AGGAATACAG   2460
ACAATTGACA  AAATTCACAG  ACTTTCAAGA  TTTTAAAAAA  CTGTTTAACA  AGGTCCCTAT   2520
TGTTACAGAT  GGAAGGGTCA  AACTTAATAA  AGGATATTTG  TTCGACTTTG  TGATTAGTTT   2580
GATGCGATTC  AAAAAAGAAT  CCTCTCTAGC  TACCACCGCA  ATAGATCCTG  TTAGATACAT   2640
AGATCCTCGT  CGCAATATCG  CATTTTCTAA  CGTGATGGAT  ATATTAAAGT  CGAATAAAGT   2700
GAACAATAAT  TAATTCTTTA  TTGTCATCAT  GAACGGCGGA  CATATTCAGT  TGATAATCGG   2760
CCCCATGTTT  TCAGGTAAAA  GTACAGAATT  AATTAGACGA  GTTAGACGTT  ATCAAATAGC   2820
TCAATATAAA  TGCGTGACTA  TAAATATTC   TAACGATAAT  AGATACGGAA  CGGGACTATG   2880
GACGCATGAT  AAGAATAATT  TTGAAGCATT  GGAAGCAACT  AAACTATGTG  ATCTCTTGGA   2940
ATCAATTACA  GATTTCTCCG  TGATAGGTAT  CGATGAAGGA  CAGTTCTTTC  AGACATTGT   3000
TGAATTCCGA  GCTTGGCTGC  AGGTCGGGGA  TCCCCCCTGC  CCGGTTATTA  TTATTTTTGA   3060
CACCAGACCA  ACTGGTAATG  GTAGCGAACG  GCGCTCAGCT  GAATTCCGCC  GATACTGACG   3120
GGCTCCAGGA  GTCGTCGCCA  CCAATCCCCA  TATGGAAACC  GTCGATATTC  AGCCATGTGC   3180
CTTCTTCCGC  GTGCAGCAGA  TGGCGATGGC  TGGTTTCCAT  CAGTTGCTGT  TGACTGTAGC   3240
GGCTGATGTT  GAACTGGAAG  TCGCCGCGCC  ACTGGTGTGG  GCCATAATTC  AATTCGCGCG   3300
TCCCGCAGCG  CAGACCGTTT  TCGCTCGGGA  AGACGTACGG  GGTATACATG  TCTGACAATG   3360
GCAGATCCCA  GCGGTCAAAA  CAGGCGGCAG  TAAGGCGGTC  GGGATAGTTT  TCTTGCGGCC   3420
CTAATCCGAG  CCAGTTTACC  CGCTCTGCTA  CCTGCGCCAG  CTGGCAGTTC  AGGCCAATCC   3480
GCGCCGGATG  CGGTGTATCG  CTCGCCACTT  CAACATCAAC  GGTAATCGCC  ATTTGACCAC   3540
TACCATCAAT  CCGGTAGGTT  TTCCGGCTGA  TAAATAAGGT  TTTCCCCTGA  TGCTGCCACG   3600
```

```
CGTGACCGGT CGTAATCAGC ACCGCATCAG CAAGTGTATC TGCCGTGCAC TGCAACAACG    3660
CTGCTTCGGC CTGGTAATGG CCCGCCGCCT TCCAGCGTTC GACCCAGGCG TTAGGGTCAA    3720
TGCGGGTCGC TTCACTTACG CCAATGTCGT TATCCAGCGG TGCACGGGTG AACTGATCGC    3780
GCAGCGGCGT CAGCAGTTGT TTTTTATCGC CAATCCACAT CTGTGAAAGA AAGCCTGACT    3840
GGCGGTTAAA TTGCCAACGC TTATTACCCA GCTCGATGCA AAAATCCATT TCGCTGGTGG    3900
TCAGATGCGG GATGGCGTGG GACGCGGCGG GGAGCGTCAC ACTGAGGTTT CCGCCAGAC    3960
GCCACTGCTG CCAGGCGCTG ATGTGCCCGG CTTCTGACCA TGCGGTCGCG TTCGGTTGCA    4020
CTACGCGTAC TGTGAGCCAG AGTTGCCCGG CGCTCTCCGG CTGCGGTAGT TCAGGCAGTT    4080
CAATCAACTG TTTACCTTGT GGAGCGACAT CCAGAGGCAC TTCACCGCTT GCCAGCGGCT    4140
TACCATCCAG CGCCACCATC CAGTGCAGGA GCTCGTTATC GCTATGACGG AACAGGTATT    4200
CGCTGGTCAC TTCGATGGTT TGCCCGGATA AACGGAACTG GAAAAACTGC TGCTGGTGTT    4260
TTGCTTCCGT CAGCGCTGGA TGCGGCGTGC GGTCGGCAAA GACCAGACCG TTCATACAGA    4320
ACTGGCGATC GTTCGGCGTA TCGCCAAAAT CACCGCCGTA AGCCGACCAC GGGTTGCCGT    4380
TTTCATCATA TTTAATCAGC GACTGATCCA CCCAGTCCCA GACGAAGCCG CCCTGTAAAC    4440
GGGGATACTG ACGAAACGCC TGCCAGTATT TAGCGAAACC GCCAAGACTG TTACCCATCG    4500
CGTGGGCGTA TTCGCAAAGG ATCAGCGGGC GCGTCTCTCC AGGTAGCGAA AGCCATTTTT    4560
TGATGGACCA TTTCGGCACA GCCGGGAAGG CTGGTCTTC ATCCACGCGC GCGTACATCG    4620
GGCAAATAAT ATCGGTGGCC GTGGTGTCGG CTCCGCCGCC TTCATACTGC ACCGGGCGGG    4680
AAGGATCGAC AGATTTGATC CAGCGATACA GCGCGTCGTG ATTAGCGCCG TGGCCTGATT    4740
CATTCCCCAG CGACCAGATG ATCACACTCG GGTGATTACG ATCGCGCTGC ACCATTCGCG    4800
TTACGCGTTC GCTCATCGCC GGTAGCCAGC GCGGATCATC GGTCAGACGA TTGATTGGCA    4860
CCATGCCGTG GGTTTCAATA TTGGCTTCAT CCACCACATA CAGGCCGTAG CGGTCGCACA    4920
GCGTGTACCA CAGCGGATGG TTCGGATAAT GCGAACAGCG CACGGCGTTA AAGTTGTTCT    4980
GCTTCATCAG CAGGATATCC TGCACCATCG TCTGCTCATC CATGACCTGA CCATGCAGAG    5040
GATGATGCTC GTGACGGTTA ACGCCTCGAA TCAGCAACGG CTTGCCGTTC AGCAGCAGCA    5100
GACCATTTTC AATCCGCACC TCGCGGAAAC CGACATCGCA GGCTTCTGCT TCAATCAGCG    5160
TGCCGTCGGC GGTGTGCAGT TCAACCACCG CACGATAGAG ATTCGGGATT CGGCGCTCC    5220
ACAGTTTCGG GTTTTCGACC TTGAGACGTA GTGTGACGCG ATCGGCATAA CCACCACGCT    5280
CATCGATAAT TTCACCGCCG AAAGGCGCGG TGCCGCTGGC GACCTGCGTT TCACCCTGCC    5340
ATAAAGAAAC TGTTACCCGT AGGTAGTCAC GCAACTCGCC GCACATCTGA ACTTCAGCCT    5400
CCAGTACAGC GCGGCTGAAA TCATCATTAA AGCGAGTGGC AACATGGAAA TCGCTGATTT    5460
GTGTAGTCGG TTTATGCAGC AACGAGACGT CACGGAAAAT GCCGCTCATC CGCCACATAT    5520
CCTGATCTTC CAGATAACTG CCGTCACTCC AACGCAGCAC CATCACCGCG AGGCGGTTTT    5580
CTCCGGCGCG TAAAAATGCG CTCAGGTCAA ATTCAGACGG CAAACGACTG TCCTGGCCGT    5640
AACCGACCCA GCGCCCGTTG CACCACAGAT GAAACGCCGA GTTAACGCCA TCAAAAATAA    5700
TTCGCGTCTG GCCTTCCTGT AGCCAGCTTT CATCAACATT AAATGTGAGC GAGTAACAAC    5760
CCGTCGGATT CTCCGTGGGA ACAAACGGCG GATTGACCGT AATGGGATAG GTTACGTTGG    5820
TGTAGATGGG CGCATCGTAA CCGTGCATCT GCCAGTTTGA GGGGACGACG ACAGTATCGG    5880
CCTCAGGAAG ATCGCACTCC AGCCAGCTTT CCGGCACCGC TTCTGGTGCC GGAAACCAGG    5940
CAAAGCGCCA TTCGCCATTC AGGCTGCGCA ACTGTTGGGA AGGGCGATCG GTGCGGGCCT    6000
```

```
CTTCGCTATT ACGCCAGCTG GCGAAAGGGG GATGTGCTGC AAGGCGATTA AGTTGGGTAA    6060
CGCCAGGGTT TTCCCAGTCA CGACGTTGTA AAACGACGGG ATCCCTCGAG GAATTCATTT    6120
ATAGCATAGA AAAAACAAA  ATGAAATTCT ACTATATTTT TACATACATA TATTCTAAAT    6180
ATGAAAGTGG TGATTGTGAC TAGCGTAGCA TCGCTTCTAG ACATATACTA TATAGTAATA    6240
CCAATACTCA AGACTACGAA ACTGATACAA TCTCTTATCA TGTGGGTAAT GTTCTCGATG    6300
TCGAATAGCC ATATGCCGGT AGTTGCGATA TACATAAACT GATCACTAAT TCCAAACCCA    6360
CCCGCTTTTT ATAGTAAGTT TTTCACCCAT AAATAATAAA TACAATAATT AATTTCTCGT    6420
AAAAGTAGAA AATATATTCT AATTTATTGC ACGGTAAGGA AGTAGAATCA TAAAGAACAG    6480
TGACGGATCC CGGGATGGCC ACACAGGGAC AACGCGTCAA CTGGGGAGAT GAACCTTCCA    6540
AAAGACGTGG TCGTTCTAAC TCTCGTGGTC GGAAGAATAA TGATATACCT TTGTCATTCT    6600
ACAACCCCAT TACCCTCGAA CAAGGATCTA AATTTTGGAA TTTATGTCCG AGAGACCTTG    6660
TTCCCAAAGG AATAGGTAAT AAGGATCAAC AAATTGGTTA TTGGAATAGA CAGATTCGTT    6720
ATCGTATTGT AAAAGGCCAG CGTAAGGAAC TCGCTGAGAG GTGGTTCTTT TACTTCTTAG    6780
GTACAGGACC TCATGCTGAT GCTAAATTCA AAGACAAGAT TGATGGAGTC TTCTGGGTTG    6840
CAAGGGATGG TGCCATGAAC AAGCCCACAA CGCTTGGCAC TCGTGGAACC AATAACGAAT    6900
CCAAACCACT GAGATTTGAT GGTAAGATAC CGCCACAGTT TCAGCTTGAA GTGAACCGTT    6960
CTAGGAACAA TTCAAGGTCT GGTTCTCAGT CTAGATCTGT TTCAAGAAAC AGATCTCAAT    7020
CTAGAGGAAG ACACCATTCC AATAACCAGA ATAATAATGT TGAGGATACA ATTGTAGCCG    7080
TGCTTGAAAA ATTAGGTGTT ACTGACAAAC AAAGGTCACG TTCTAAACCT AGAGAACGTA    7140
GTGATTCCAA ACCTAGGGAC ACAACACCTA AGAATGCCAA CAAACACACC TGGAAGAAAA    7200
CTGCAGGCAA GGGAGATGTG ACAACTTTCT ATGGTGCTAG AAGTAGTTCA GCTAACTTTG    7260
GTGATAGTGA TCTCGTTGCC AATGGTAACG CTGCCAAATG CTACCCTCAG ATAGCTGAAT    7320
GTGTTCCATC AGTGTCTAGC ATAATCTTTG GCAGTCAATG GTCTGCTGAA GAAGCTGGTG    7380
ATCAAGTGAA AGTCACGCTC ACTCACACCT ACTACCTGCC AAAGGATGAT GCCAAAACTA    7440
GTCAATTCCT AGAACAGATT GACGCTTACA AGCGACCTTC TGAAGTGGCT AAGGATCAGA    7500
GGCAAGAAG  ATCCCGTTCT AAGTCTGCTG ATAAGAAGCC TGAGGAGTTG TCTGTAACTC    7560
TTGTGGAGGC ATACACAGAT GTGTTTGATG ACACACAGGT TGAGATGATT GATGAGGTTA    7620
CGAACTAAAC GCATGCCCGG GAATTCTGTG AGCGTATGGC AAACGAAGGA AAAATTAGTT    7680
ATAGTAGCCG CACTCGATGG GACATTTCAA CGTAAACCGT TTAATAATAT TTTGAATCTT    7740
ATTCCATTAT CTGAAATGGT GGTAAAACTA ACTGCTGTGT GTATGAAATG CTTTAAGGAG    7800
GCTTCCTTTT CTAAACGATT GGGTGAGGAA ACCGAGATAG AAATAATAGG AGGTAATGAT    7860
ATGTATCAAT CGGTGTGTAG AAAGTGTTAC ATCGACTCAT AATATTATAT TTTTATCTA    7920
AAAAACTAAA AATAAACATT GATTAAATTT TAATATAATA CTTAAAAATG GATGTTGTGT    7980
CGTTAGATAA ACCGTTTATG TATTTTGAGG AAATTGATAA TGAGTTAGAT TACGAACCAG    8040
AAAGTGCAAA TGAGGTCGCA AAAAACTGC CGTATCAAGG ACAGTTAAAA CTATTACTAG    8100
GAGAATTATT TTTTCTTAGT AAGTTACAGC GACACGGTAT ATTAGATGGT GCCACCGTAG    8160
TGTATATAGG ATCTGCTCCC GGTACACATA TACGTTATTT GAGAGATCAT TTCTATAATT    8220
TAGGAGTGAT CATCAAATGG ATGCTAATTG ACGGCCGCCA TCATGATCCT ATTTTAAATG    8280
GATTGCGTGA TGTGACTCTA GTGACTCGGT TCGTTGATGA GGAATATCTA CGATCCATCA    8340
AAAAACAACT GCATCCTTCT AAGATTATTT TAATTTCTGA TGTGAGATCC AAACGAGGAG    8400
```

-continued

```
GAAATGAACC TAGTACGGCG GATTTACTAA GTAATTACGC TCTACAAAAT GTCATGATTA   8460
GTATTTTAAA CCCCGTGGCG TCTAGTCTTA AATGGAGATG CCCGTTTCCA GATCAATGGA   8520
TCAAGGACTT TTATATCCCA CACGGTAATA AAATGTTACA ACCTTTTGCT CCTTCATATT   8580
CAGGGCCGTC GTTTTACAAC GTCGTGACTG GGAAAACCCT GGCGTTACCC AACTTAATCG   8640
CCTTGCAGCA CATCCCCCTT TCGCCAGCTG GCGTAATAGC GAAGAGGCCC GCACCGATCG   8700
CCCTTCCCAA CAGTTGCGCA GCCTGAATGG CGAATGGCGC CTGATGCGGT ATTTTCTCTT   8760
TACGCATCTG TGCGGTATTT CACACCGCAT ATGGTGCACT CTCAGTACCA TCTGCTCTGA   8820
TGCCGCATAG TTAAGCCAGT ACACTCCGCT ATCGCTACGT GACTGGGTCA TGGCTGCGCC   8880
CCGACACCCG CCAACACCCG CTGACGCGCC CTGACGGGCT TGTCTGCTCC CGGCATCCGC   8940
TTACAGACAA GCTGTGACCG TCTCCGGGAG CTGCATGTGT CAGAGGTTTT CACCGTCATC   9000
ACCGAAACGC GCGAGGCAG                                                9019
```

( 2 ) INFORMATION FOR SEQ ID NO:5:

( i ) SEQUENCE CHARACTERISTICS:
( A ) LENGTH: 262 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
( A ) ORGANISM: Feline infectious peritonitis virus ( v i i ) IMMEDIATE SOURCE:
( B ) CLONE: FIPV E1

( x i ) SEQUENCE DESCRIPTION: SEQ ID NO:5:

```
Met Lys Tyr Ile Leu Leu Ile Leu Ala Cys Ile Ile Ala Cys Val Tyr
 1               5                  10                  15
Gly Glu Arg Tyr Cys Ala Met Gln Asp Ser Gly Leu Gln Cys Ile Asn
            20                  25                  30
Gly Thr Asn Ser Arg Cys Gln Thr Cys Phe Glu Arg Gly Asp Leu Ile
        35                  40                  45
Trp His Leu Ala Asn Trp Asn Phe Ser Trp Ser Val Ile Leu Ile Val
    50                  55                  60
Phe Ile Thr Val Leu Gln Tyr Gly Arg Pro Gln Phe Ser Trp Leu Val
65                  70                  75                  80
Tyr Gly Ile Lys Met Leu Ile Met Trp Leu Leu Trp Pro Ile Val Leu
                85                  90                  95
Ala Leu Thr Ile Phe Asn Ala Tyr Ser Glu Tyr Gln Val Ser Arg Tyr
            100                 105                 110
Val Met Phe Gly Phe Ser Val Ala Gly Ala Val Val Thr Phe Ala Leu
        115                 120                 125
Trp Met Met Tyr Phe Val Arg Ser Val Gln Leu Tyr Arg Arg Thr Lys
    130                 135                 140
Ser Trp Trp Ser Phe Asn Pro Glu Thr Asn Ala Ile Leu Cys Val Asn
145                 150                 155                 160
Ala Leu Gly Arg Ser Tyr Val Leu Pro Leu Asp Gly Thr Pro Thr Gly
                165                 170                 175

```
Val  Thr  Leu  Thr  Leu  Leu  Ser  Gly  Asn  Leu  Tyr  Ala  Glu  Gly  Phe  Lys
               180                      185                    190

Met  Ala  Gly  Gly  Leu  Thr  Ile  Glu  His  Leu  Pro  Lys  Tyr  Val  Met  Ile
          195                      200                    205

Ala  Thr  Pro  Ser  Arg  Thr  Ile  Val  Tyr  Thr  Leu  Val  Gly  Lys  Gln  Leu
     210                      215                    220

Lys  Ala  Thr  Thr  Ala  Thr  Gly  Trp  Ala  Tyr  Tyr  Val  Lys  Ser  Lys  Ala
225                           230                    235                    240

Gly  Asp  Tyr  Ser  Thr  Glu  Ala  Arg  Thr  Asp  Asn  Leu  Ser  Glu  His  Glu
               245                      250                    255

Lys  Leu  Leu  His  Met  Val
               260
```

( 2 ) INFORMATION FOR SEQ ID NO:6:

( i ) SEQUENCE CHARACTERISTICS:
        ( A ) LENGTH: 377 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Feline infectious peritonitis virus ( v i i ) IMMEDIATE SOURCE:
        ( B ) CLONE: FIPV N ( x i ) SEQUENCE DESCRIPTION: SEQ ID NO:6:

```
Met  Ala  Thr  Gln  Gly  Gln  Arg  Val  Asn  Trp  Gly  Asp  Glu  Pro  Ser  Lys
 1                  5                      10                         15

Arg  Arg  Gly  Arg  Ser  Asn  Ser  Arg  Gly  Arg  Lys  Asn  Asn  Asp  Ile  Pro
               20                      25                    30

Leu  Ser  Phe  Tyr  Asn  Pro  Ile  Thr  Leu  Glu  Gln  Gly  Ser  Lys  Phe  Trp
          35                      40                    45

Asn  Leu  Cys  Pro  Arg  Asp  Leu  Val  Pro  Lys  Gly  Ile  Gly  Asn  Lys  Asp
     50                      55                    60

Gln  Gln  Ile  Gly  Tyr  Trp  Asn  Arg  Gln  Ile  Arg  Tyr  Arg  Ile  Val  Lys
65                       70                    75                         80

Gly  Gln  Arg  Lys  Glu  Leu  Ala  Glu  Arg  Trp  Phe  Phe  Tyr  Phe  Leu  Gly
               85                      90                    95

Thr  Gly  Pro  His  Ala  Asp  Ala  Lys  Phe  Lys  Asp  Lys  Ile  Asp  Gly  Val
               100                     105                   110

Phe  Trp  Val  Ala  Arg  Asp  Gly  Ala  Met  Asn  Lys  Pro  Thr  Thr  Leu  Gly
          115                     120                   125

Thr  Arg  Gly  Thr  Asn  Asn  Glu  Ser  Lys  Pro  Leu  Arg  Phe  Asp  Gly  Lys
     130                     135                   140

Ile  Pro  Pro  Gln  Phe  Gln  Leu  Glu  Val  Asn  Arg  Ser  Arg  Asn  Asn  Ser
145                      150                   155                       160

Arg  Ser  Gly  Ser  Gln  Ser  Arg  Ser  Val  Ser  Arg  Asn  Arg  Ser  Gln  Ser
               165                     170                   175

Arg  Gly  Arg  His  His  Ser  Asn  Asn  Gln  Asn  Asn  Asn  Val  Glu  Asp  Thr
               180                     185                   190
```

|     |     |     |     |     |     |     |     |     |     |     |     |     |     |     |
|-----|-----|-----|-----|-----|-----|-----|-----|-----|-----|-----|-----|-----|-----|-----|
| Ile | Val | Ala | Val | Leu | Glu | Lys | Leu | Gly | Val | Thr | Asp | Lys | Gln | Arg | Ser |
|     |     | 195 |     |     |     |     | 200 |     |     |     |     | 205 |     |     |
| Arg | Ser | Lys | Pro | Arg | Glu | Arg | Ser | Asp | Ser | Lys | Pro | Arg | Asp | Thr | Thr |
|     | 210 |     |     |     |     | 215 |     |     |     |     | 220 |     |     |     |
| Pro | Lys | Asn | Ala | Asn | Lys | His | Thr | Trp | Lys | Lys | Thr | Ala | Gly | Lys | Gly |
| 225 |     |     |     |     | 230 |     |     |     |     | 235 |     |     |     |     | 240 |
| Asp | Val | Thr | Thr | Phe | Tyr | Gly | Ala | Arg | Ser | Ser | Ser | Ala | Asn | Phe | Gly |
|     |     |     |     | 245 |     |     |     |     | 250 |     |     |     |     | 255 |     |
| Asp | Ser | Asp | Leu | Val | Ala | Asn | Gly | Asn | Ala | Ala | Lys | Cys | Tyr | Pro | Gln |
|     |     |     | 260 |     |     |     |     | 265 |     |     |     |     | 270 |     |     |
| Ile | Ala | Glu | Cys | Val | Pro | Ser | Val | Ser | Ser | Ile | Ile | Phe | Gly | Ser | Gln |
|     |     | 275 |     |     |     |     | 280 |     |     |     |     | 285 |     |     |     |
| Trp | Ser | Ala | Glu | Glu | Ala | Gly | Asp | Gln | Val | Lys | Val | Thr | Leu | Thr | His |
|     | 290 |     |     |     |     | 295 |     |     |     |     | 300 |     |     |     |     |
| Thr | Tyr | Tyr | Leu | Pro | Lys | Asp | Asp | Ala | Lys | Thr | Ser | Gln | Phe | Leu | Glu |
| 305 |     |     |     |     | 310 |     |     |     |     | 315 |     |     |     |     | 320 |
| Gln | Ile | Asp | Ala | Tyr | Lys | Arg | Pro | Ser | Glu | Val | Ala | Lys | Asp | Gln | Arg |
|     |     |     |     | 325 |     |     |     |     | 330 |     |     |     |     | 335 |     |
| Gln | Arg | Arg | Ser | Arg | Ser | Lys | Ser | Ala | Asp | Lys | Lys | Pro | Glu | Glu | Leu |
|     |     |     | 340 |     |     |     |     | 345 |     |     |     |     | 350 |     |     |
| Ser | Val | Thr | Leu | Val | Glu | Ala | Tyr | Thr | Asp | Val | Phe | Asp | Asp | Thr | Gln |
|     |     | 355 |     |     |     |     | 360 |     |     |     |     | 365 |     |     |     |
| Val | Glu | Met | Ile | Asp | Glu | Val | Thr | Asn |     |     |     |     |     |     |     |
|     |     | 370 |     |     |     |     | 375 |     |     |     |     |     |     |     |     |

( 2 ) INFORMATION FOR SEQ ID NO:7:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: Other nucleic acid ( v i ) ORIGINAL SOURCE:
        ( A ) ORGANISM: Feline infectious peritonitis virus ( v i i ) IMMEDIATE SOURCE:
        ( B ) CLONE: N primer #1

( x i ) SEQUENCE DESCRIPTION: SEQ ID NO:7:

CTCGTGGTCG GAAGAATAAT GATA    24

( 2 ) INFORMATION FOR SEQ ID NO:8:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: Other nucleic acid ( v i ) ORIGINAL SOURCE:
        ( A ) ORGANISM: Feline infectious peritonitis virus ( v i i ) IMMEDIATE SOURCE:
        ( B ) CLONE: N primer #2

( x i ) SEQUENCE DESCRIPTION: SEQ ID NO:8:

AGCACCATAG AAAGTTGTCA CATC    24

( 2 ) INFORMATION FOR SEQ ID NO:9:

-continued ( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: Other nucleic acid ( v i ) ORIGINAL SOURCE:
( A ) ORGANISM: Feline infectious peritonitis virus ( v i i ) IMMEDIATE SOURCE:
( B ) CLONE: E1 primer #1

( x i ) SEQUENCE DESCRIPTION: SEQ ID NO:9:

TATGTAATGT TCGGCTTTAG TG 22

( 2 ) INFORMATION FOR SEQ ID NO:10:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: Other nucleic acid ( v i ) ORIGINAL SOURCE:
( A ) ORGANISM: Feline infectious peritonitis virus ( v i i ) IMMEDIATE SOURCE:
( B ) CLONE: E1 primer #2

( x i ) SEQUENCE DESCRIPTION: SEQ ID NO:10:

GTGCTTCTGT TGAGTAATCA CC 22

What is claimed is:

1. A recombinant raccoon poxvirus having at least one internal gene comprising a DNA sequence encoding the nucleocapsid (N) protein of Feline Infectious Peritonitis Virus (FIPV).

2. The recombinant raccoon poxvirus of claim 1 wherein said internal gene has the amino acid sequence of SEQ ID NO: 6.

3. A vaccine comprising:

a recombinant raccoon poxvirus having at least one internal gene comprising a DNA sequence encoding the nucleocapsid (N) protein of Feline Infectious Peritonitis Virus (FIPV), and a pharmaceutically acceptable carrier.

4. The vaccine of claim 3 wherein said internal gene has the amino acid sequence of SEQ ID NO: 6.

5. The vaccine of claim 3 further comprising inactivated or attenuated viruses selected from the group consisting of feline leukemia virus, feline panleucopenia virus, feline rhinotracheitis virus, feline calicivirus, feline immunodeficiency virus, feline herpesvirus, feline enteric coronavirus, and mixtures thereof.

6. The vaccine of claim 3 further comprising organisms selected from the group consisting of inactivated or attenuated feline *Chlamydia psittaci, Microsporum canis*, and mixtures thereof.

7. The vaccine of claim 3, further comprising a pharmaceutically acceptable adjuvant.

8. A method for preventing disease caused by Feline Infectious Peritonitis Virus (FIPV), comprising administering to a feline in need of such treatment via a subcutaneous or intramuscular route a vaccine comprising a recombinant raccoon poxvirus having at least one internal gene comprising a DNA sequence encoding the nucleocapsid (N) protein of FIPV.

9. The method of claim 8 wherein said internal gene has the amino acid sequence of SEQ ID NO: 6.

* * * * *